United States Patent
Cheung et al.

(10) Patent No.: US 9,211,304 B2
(45) Date of Patent: Dec. 15, 2015

(54) THERAPY-ENHANCING GLUCAN

(71) Applicants: SLOAN-KETTERING INSTITUTE FOR CANCER RESEARCH, New York, NY (US); Biotec Pharmacon ASA, Oslo (NO)

(72) Inventors: Nai-Kong V. Cheung, New York, NY (US); Rolf Einar Engstad, Tromosø (NO)

(73) Assignees: Sloan-Kettering Institute for Cancer Research, New York, NY (US); BIOTEC PHARMACON ASA, Oslo (NO)

( * ) Notice: Subject to any disclaimer, the term of this patent is extended or adjusted under 35 U.S.C. 154(b) by 298 days.

(21) Appl. No.: 13/760,307

(22) Filed: Feb. 6, 2013

(65) Prior Publication Data

US 2013/0183295 A1  Jul. 18, 2013

Related U.S. Application Data

(63) Continuation of application No. 12/767,237, filed on Apr. 26, 2010, now abandoned, which is a continuation of application No. 10/565,484, filed as application No. PCT/US2004/023099 on Jul. 16, 2004, now Pat. No. 7,704,973, which is a continuation-in-part of application No. 10/621,027, filed on Jul. 16, 2003, now Pat. No. 7,507,724.

(51) Int. Cl.
| | | |
|---|---|---|
| A61K 31/716 | (2006.01) | |
| C08B 37/00 | (2006.01) | |
| A61K 31/715 | (2006.01) | |
| A61K 31/739 | (2006.01) | |
| A61K 39/39 | (2006.01) | |
| A61K 39/395 | (2006.01) | |
| A61K 39/44 | (2006.01) | |
| A61K 47/36 | (2006.01) | |
| A61K 39/00 | (2006.01) | |

(52) U.S. Cl.
CPC ............ *A61K 31/716* (2013.01); *A61K 31/715* (2013.01); *A61K 31/739* (2013.01); *A61K 39/39* (2013.01); *A61K 39/39541* (2013.01); *A61K 39/39558* (2013.01); *A61K 39/44* (2013.01); *A61K 47/36* (2013.01); *C08B 37/0024* (2013.01); *A61K 2039/55583* (2013.01)

(58) Field of Classification Search
None
See application file for complete search history.

(56) References Cited

U.S. PATENT DOCUMENTS

| | | |
|---|---|---|
| 3,975,553 A | 8/1976 | Griffon |
| 3,987,166 A | 10/1976 | Komatsu et al. |
| 4,251,519 A | 2/1981 | Robbins et al. |
| 4,343,784 A | 8/1982 | Massot et al. |
| 4,454,289 A | 6/1984 | Nakajima et al. |
| 4,705,780 A | 11/1987 | Massot et al. |
| 4,761,402 A | 8/1988 | Williams et al. |
| 4,810,646 A | 3/1989 | Jamas et al. |
| 4,818,752 A | 4/1989 | Williams et al. |
| 4,833,131 A | 5/1989 | Williams et al. |
| 4,900,722 A | 2/1990 | Williams et al. |
| 4,926,094 A | 5/1990 | Bondeson et al. |
| 4,992,540 A | 2/1991 | Jamas et al. |
| 5,032,401 A | 7/1991 | Jamas et al. |
| 5,037,972 A | 8/1991 | Jamas et al. |
| 5,130,127 A | 7/1992 | Herlyn |
| 5,189,028 A | 2/1993 | Nikl et al. |
| 5,223,491 A | 6/1993 | Donzis |
| 5,250,436 A | 10/1993 | Jamas et al. |
| 5,322,841 A * | 6/1994 | Jamas et al. .................... 514/54 |
| 5,504,079 A | 4/1996 | Jamas et al. |
| 5,519,009 A | 5/1996 | Donzis |
| 5,532,223 A | 7/1996 | Jamas et al. |
| 5,576,015 A | 11/1996 | Donzis |
| 5,607,677 A | 3/1997 | Jamas et al. |
| 5,610,280 A | 3/1997 | Brandt et al. |
| 5,614,242 A | 3/1997 | Fox |
| 5,622,939 A | 4/1997 | Jamas et al. |
| 5,622,940 A | 4/1997 | Ostroff |
| 5,696,079 A | 12/1997 | Lane et al. |

(Continued)

FOREIGN PATENT DOCUMENTS

| | | |
|---|---|---|
| DE | 30 19 614 A1 | 12/1981 |
| EP | 0194851 | 9/1986 |

(Continued)

OTHER PUBLICATIONS

Rosell et al., "Molecular markers and targeted therapy with novel agents: prospects in the treatment of non-small cell lung cancer" Jung Cancer 38 (2002) pp. S43-S49.*

(Continued)

*Primary Examiner* — Eric Olson
(74) *Attorney, Agent, or Firm* — Law Offices of Albert Wai-Kit Chan, PLLC

(57) ABSTRACT

This invention provides a method for introducing substances into cells comprising contacting a composition comprising orally administered beta-glucan with said cells. This invention also provides a method for introducing substances into a subject comprising administering to the subject an effective amount of the above compositions. The substance which could be delivered orally includes but is not limited to peptides, proteins, RNAs, DNAs, chemotherapeutic agents, biologically active agents, plasmids, and other small molecules and compounds. Finally, this invention provides a composition comprising orally administered beta-glucan capable of enhancing efficacy of IgM and different uses of the said composition.

20 Claims, 14 Drawing Sheets

(56) References Cited

U.S. PATENT DOCUMENTS

| | | | |
|---|---|---|---|
| 5,702,719 A | 12/1997 | Donzis | |
| 5,726,023 A | 3/1998 | Cheever et al. | |
| 5,736,137 A | 4/1998 | Anderson et al. | |
| 5,741,495 A | 4/1998 | Jamas et al. | |
| 5,783,569 A * | 7/1998 | Jamas et al. | 514/54 |
| 5,804,199 A | 9/1998 | Aasjord et al. | |
| 5,811,542 A | 9/1998 | Jamas et al. | |
| 5,817,643 A | 10/1998 | Jamas et al. | |
| 5,849,720 A | 12/1998 | Jamas et al. | |
| 5,935,821 A | 8/1999 | Chatterjee et al. | |
| 5,980,918 A | 11/1999 | Klein | |
| 6,020,324 A | 2/2000 | Jamas et al. | |
| 6,117,850 A | 9/2000 | Patchen et al. | |
| 6,143,731 A | 11/2000 | Jamas et al. | |
| 6,143,883 A | 11/2000 | Lehmann et al. | |
| 6,217,866 B1 | 4/2001 | Schlessinger et al. | |
| 6,369,216 B1 | 4/2002 | Patchen et al. | |
| 6,573,245 B1 | 6/2003 | Marciani | |
| 6,664,370 B2 | 12/2003 | Cheever | |
| 7,011,845 B2 | 3/2006 | Kozbor et al. | |
| 7,030,101 B2 | 4/2006 | Pavliak et al. | |
| 7,070,778 B2 | 7/2006 | Yvin et al. | |
| 8,791,252 B2 * | 7/2014 | Cheung | 536/123.12 |
| 2002/0044919 A1 | 4/2002 | Yu | |
| 2002/0119928 A1 | 8/2002 | McAnalley | |
| 2002/0160014 A1 | 10/2002 | Rodriguez et al. | |
| 2003/0180254 A1 | 9/2003 | Lane et al. | |
| 2004/0109857 A1 | 6/2004 | Chu et al. | |
| 2004/0116379 A1 | 6/2004 | Cheung | |
| 2004/0142000 A1 | 7/2004 | Suga et al. | |
| 2004/0248772 A1 | 12/2004 | Yagita | |
| 2004/0266726 A1 | 12/2004 | Yagita | |
| 2005/0118187 A1 | 6/2005 | Yu | |
| 2005/0208079 A1 | 9/2005 | Cassone et al. | |
| 2006/0009419 A1 | 1/2006 | Ross et al. | |
| 2006/0020128 A1 | 1/2006 | Cheung | |
| 2006/0160766 A1 | 7/2006 | Cheung | |
| 2006/0165700 A1 * | 7/2006 | Ostroff et al. | 424/155.1 |
| 2006/0263355 A1 | 11/2006 | Quan et al. | |
| 2007/0020232 A1 | 1/2007 | Rossignol et al. | |
| 2007/0059310 A1 | 3/2007 | Karel | |
| 2007/0134259 A1 | 6/2007 | Bundle et al. | |
| 2009/0053221 A1 | 2/2009 | Cheung et al. | |

FOREIGN PATENT DOCUMENTS

| | | |
|---|---|---|
| EP | 046350 A1 | 2/1992 |
| EP | 0759089 B1 | 4/1995 |
| JP | 62252730 | 11/1987 |
| JP | 63-500805 | 3/1988 |
| JP | 63307825 | 12/1988 |
| WO | 91/03248 | 3/1991 |
| WO | 95/30022 | 11/1995 |
| WO | 97/35619 | 10/1997 |
| WO | 98/39013 | 9/1998 |
| WO | 99/52548 | 10/1999 |
| WO | 00/15238 | 3/2000 |
| WO | 01/56601 | 8/2001 |
| WO | 01/62283 | 8/2001 |
| WO | 01/68105 | 11/2001 |
| WO | 01/80807 | 11/2001 |
| WO | 02/058711 | 8/2002 |
| WO | 03/004507 | 1/2003 |
| WO | 03/054077 | 7/2003 |
| WO | 2004/014320 | 2/2004 |
| WO | 2004/021994 | 3/2004 |
| WO | 2004/030613 | 3/2004 |
| WO | WO2004/021994 * | 3/2004 |
| WO | 2005/027936 | 3/2005 |
| WO | 2005/027938 | 3/2005 |
| WO | 2005/049044 | 6/2005 |
| WO | 2006/007372 | 1/2006 |
| WO | 2006/085895 | 8/2006 |
| WO | 2006/119395 | 11/2006 |
| WO | 2007/084661 | 7/2007 |

OTHER PUBLICATIONS

The Oxford Textbook of Oncology, 1995, published by Oxford University Press, pp. 447-453.*
2006 chemical abstracts catalog, "STN database descriptions", published 2006 by chemical abstracts service, p. 52.*
Australian Office Action, Oct. 27, 2009, for Sloan-Kettering Institute for Cancer Research, Australian Application No. 2008207369, Filed Aug. 18, 2008, Continuation-In-Part of PCT/US07/01427, Filed Jan. 17, 2007.
Australian Office Action, Jun. 12, 2009, for Sloan-Kettering Institute for Cancer Research, Australian Application No. 2008207369, Filed Aug. 18, 2008, continuation-in-part of PCT/US07/01427.
Australian Office Action, Dec. 4, 2008, for Sloan-Kettering Institute for Cancer Research and Biotec Pharmacon ASA, Australian Application No. 2008207369 Filed Aug. 18, 2008, corresponding to PCT/US2007/001427.
Canadian Office Action, Jan. 25, 2010, for Sloan-Kettering Institute for Cancer Research, Canadian Application No. 2,434,938, Filed Jul. 15, 2003, National Stage of PCT/US02/01276, Filed Jan. 15, 2002.
Canadian Office Action, Oct. 29, 2009, for Sloan-Kettering Institute for Cancer Research, Canadian Application No. 2,536,632, Filed Jan. 13, 2006, National Stage of PCT/US04/23099, Filed Jul. 16, 2004.
Canadian Office Action, Mar. 26, 2009, for Sloan-Kettering Institute for Cancer Research, Canadian Application No. 2,434,938, Filed Jul. 15, 2003, National Stage of PCT/US02/01276.
Chinese Office Action, Jul. 24, 2009, for Sloan-Kettering Institute for Cancer Research, Chinese Application No. 200480020356.6, Filed Jan. 16, 2006, National Stage of PCT/US04/23099.
Chinese Office Action, Feb. 27, 2009, for Sloan-Kettering Institute for Cancer Research, Chinese Application No. 200480020356.6, Filed Jan. 16, 2006, National Stage of PCT/US04/23099.
Chinese Rejection Decision, Jan. 29, 2010, for Sloan-Kettering Institute for Cancer Research, Chinese Application No. 200480020356.6, Filed Jan. 16, 2006, National Stage of PCT/US04/23099, Filed Jul. 16, 2004. (with English translation).
Chinese Office Action, Oct. 31, 2008, for Sloan-Kettering Institute for Cancer Research, Chinese Application No. 200480020356.6, Filed Jan. 16, 2006, corresponding to PCT/US04/23099.
European Office Action, Mar. 30, 2009, for Sloan-Kettering Institute for Cancer Research, European Application No. 02 707 502.7, Filed Aug. 4, 2003, National Stage of PCT/US02/01276.
European Office Action, Oct. 21, 2009, for Sloan-Kettering Institute for Cancer Research, European Application No. 02 707 502.7, Filed Aug. 4, 2003, National Stage of PCT/US02/01276, Filed Jan. 15, 2002.
Supplementary European Search Report, Dec. 11, 2009, for Sloan-Kettering Institute for Cancer Research, European Application No. EP 04786081.
Supplementary Partial European Search Report, Feb. 5, 2008, for European Application No. EP 02 70 7502, filed Aug. 4, 2003 for Sloan-Kettering Institute for Cancer Research.
Indian First Examination Report, Feb. 12, 2009, for Sloan-Kettering Institute for Cancer Research, Indian Application No. 186/MUMNP/2006, Filed Feb. 15, 2006, corresponding to PCT/US04/23099.
Mexican Office Action, Sep. 18, 2009, for Sloan-Kettering Institute for Cancer Research, Mexican Application No. PA/a/2006/000615, Filed Jan. 16, 2006, National Stage of PCT/US04/23099, Filed Jul. 16, 2004. (with English translation).
Mexican Office Action, May 29, 2009, for Sloan-Kettering Institute for Cancer Research, Mexican Application No. PA/a/2006/000615, Filed Jul. 16, 2004, National Stage of PCT/US04/23099.
PCT International Search Report for Sloan-Kettering Institute for Cancer Research, Sep. 26, 2007, Int'l Application No. PCT/US07/01427, Filed Jan. 18, 2007.
PCT Written Opinion of the International Searching Authority for Sloan-Kettering Institute for Cancer Research, Sep. 26, 2007, Int'l Application No. PCT/US07/01427, Filed Jan. 18, 2007.

(56) References Cited

OTHER PUBLICATIONS

U.S. Office Action, Nov. 10, 2009, for Nai-Kong V. Cheung, U.S. Appl. No. 12/161,285, filed Jul. 17, 2008.
U.S. Office Action, Nov. 12, 2009, for Nai-Kong V. Cheung, U.S. Appl. No. 12/212,352, filed Sep. 17, 2008.
U.S. Advisory Action, Aug. 6, 2009, for Nai-Kong V. Cheung, U.S. Appl. No. 12/036,462, filed Feb. 25, 2008.
U.S. Advisory Action, Jul. 10, 2009, for Nai-Kong V. Cheung, U.S. Appl. No. 12/036,462, filed Feb. 25, 2008.
U.S. Office Action, Jun. 2, 2009, for Nai-Kong V. Cheung, U.S. Appl. No. 11/334,763, filed, Jan. 17, 2006.
U.S. Office Action, Apr. 17, 2009, for Nai-Kong V. Cheung, U.S. Appl. No. 12/036,462, filed Feb. 25, 2008.
Chinese Office Action, May 9, 2008, for Sloan-Kettering Institute for Cancer Research, Chinese Application No. 200480020356.6, Filed Jan. 16, 2006, corresponding to PCT/US04/23099.
U.S. Office Action, Mar. 5, 2008, for Nai-Kong V. Cheung, U.S. Appl. No. 11/334,763, filed Jan. 17, 2006.
U.S. Office Action, Aug. 7, 2007, for Nai-Kong V. Cheung, U.S. Appl. No. 11/218,044, filed Aug. 31, 2005.
U.S. Office Action, Aug. 7, 2007, for Nai-Kong V. Cheung, U.S. Appl. No. 10/621,027, filed Jul. 16, 2003.
U.S. Office Action, Jan. 4, 2007, for Nai-Kong V. Cheung, U.S. Appl. No. 10/621,027, filed Jul. 16, 2003.
U.S. Office Action, Nov. 22, 2006, for Nai-Kong V. Cheung, U.S. Appl. No. 11/218,044, filed Aug. 31, 2005.
U.S. Office Action, Mar. 10, 2006, for Nai-Kong V. Cheung, U.S. Appl. No. 11/218,044, filed Aug. 31, 2005.
U.S. Office Action, Mar. 6, 2006, for Nai-Kong V. Cheung, U.S. Appl. No. 10/621,027, filed Jul. 16, 2003.
U.S. Office Action, Jul. 13, 2005, for Nai-Kong V. Cheung, U.S. Appl. No. 10/621,027, filed Jul. 16, 2003.
U.S. Office Action, Dec. 17, 2004, for Nai-Kong V. Cheung, U.S. Appl. No. 10/621,027, filed Jul. 16, 2003.
Beta Glucan Health Center webpage, Nov. 10, 2000, "PLEURAN—Beta-1,3/1-6-Glucan," http://www.glucan.com/therapy/therapy.com.
1999 The Merck Manual of Diagnosis and Therapy, 397-398, 948-949, 1916, 1979-1981.
PCT International Preliminary Examination Report for Sloan-Kettering Institute for Cancer Research, Int'l Application No. PCT/US02/01276, Filed Jan. 15, 2002, Dated Mar. 27, 2003.
PCT International Search Report for Sloan-Kettering Institute for Cancer Research, Int'l Application No. PCT/US04/23099, Filed Jul. 16, 2004, Dated Feb. 28, 2005.
PCT International Search Report for Sloan-Kettering Institute for Cancer Research, Int'l Application No. PCT/US04/23099, Filed Jul. 16, 2004, Dated Apr. 14, 2005.
PCT Written Opinion of the International Searching Authority for Sloan-Kettering Institute for Cancer Research, Int'l Application No. PCT/US04/23099, Filed Jul. 16, 2004, Dated Apr. 14, 2005.
PCT International Search Report for Sloan-Kettering Institute for Cancer Research, Int'l Application No. PCT/US02/01276, Filed Jan. 15, 2002, Dated Jun. 5, 2002.
PCT Written Opinion for Sloan-Kettering Institute for Cancer Research, et al, Int'l Application No. PCT/US02/01276, Filed Jan. 15, 2002, Dated Nov. 25, 2002.
PCT International Preliminary Report on Patentability for Sloan-Kettering Institute for Cancer Research, et al., Int'l Application No. PCT/US2004/023099, Filed Jul. 16, 2004, Dated Jan. 26, 2006.
PCT Corrected Written Opinion of the International Searching Authority for Sloan-Kettering Institute for Cancer Research, et al, Int'l Application No. PCT/US04/23099, Filed Jul. 16, 2004, Dated Aug. 10, 2005.
PCT Corrected International Search Report for Sloan-Kettering Institute for Cancer Research, et al, Int'l Application No. PCT/US2004/23099, Filed Jul. 16, 2004, Dated Aug. 10, 2005.
Search Report prepared by the Norwegian Patent Office, dated May 4, 2005.

Arturson, G.: Wallenius, G., "The Renal Clearance of Dextran of Different Molecular Sizes in Normal Humans", Scandinaz J. Clin & Lab Investigation, vol. 1, pp. 81-86 (1964).
Cheung, N.; Modak, S., "Oral (1•3),(1•4)-β-D-Glucan Synergizes with Antiganglioside GD2 Monoclonal Antibody 3F8 in the Therapy of Neuroblastoma", Clinical Cancer Research, vol. 8, pp. 1217-1223 (2002).
Cheung, N.K. et al., "Orally administered β-glucans enhance antitumor effects of monoclonal antibodies", Cancer Immunol Immunother. Nov. 2002; 51(10):557-564.
Hanaue, H. et al., "Basic Studies on Oral Administration of Lentinan (I)", J. Jpn. Soc. Cancer Ther., vol. 8, pp. 1566-1571(1989).
Oxford Textbook of Oncology, 1995, "Chemotherapy: General Aspects", Peckham, Pinedo and Veronesi, ed., vol. 1, 447-453.
Canadian Office Action, May 31, 2010, for Sloan-Kettering Institute for Cancer Research, Canadian Application 2,536,632, Filed Jan. 13, 2006, National Stage of PCT/US04/23099, Filed Jul. 16, 2004.
Canadian Office Action, Dec. 6, 2010, for Sloan-Kettering Institute for Cancer Research, Canadian Application No. 2,434,938, Filed Jul. 15, 2003, National Stage of PCT/US02/01276, Filed Jan. 15, 2002.
European Office Action, Jan. 25, 2011, for Sloan-Kettering Institute for Cancer Research, European Application No. 02 707 502.7, Filed Aug. 4, 2003, National Stage of PCT/US02/01276, Filed Jan. 15, 2002.
European Office Action, Apr. 6, 2010, for Sloan-Kettering Institute for Cancer Research, European Application No. 04786081.2, Filed Apr. 18, 2006, National Stage of PCT/US04/23099, Filed Jul. 16, 2004.
Japanese Office Action, Jan. 7, 2011, for Sloan-Kettering Institute for Cancer Research, Japanese Application No. 2006-520398, Filed Jan. 16, 2006, national stage of Int'l App'l No. PCT/US04/23099, Filed Jul. 16, 2004.
Mexican Office Action, Mar. 25, 2010, for Sloan-Kettering Institute for Cancer Research, Mexican Application No. PA/a/2006/000615, Filed Jan. 16, 2006, National Stage of PCT/US04/23099, Filed Jul. 16, 2004. (with English translation).
U.S. Office Action, Feb. 22, 2008, for Nai-Kong V. Cheung, U.S. Appl. No. 10/565,484, filed Jan. 17, 2006.
U.S. Office Action, Aug. 11, 2008, for Nai-Kong V, Cheung, U.S. Appl. No. 10/565,484, filed Jan. 17, 2006.
U.S. Office Action, Oct. 24, 2008, for Nai-Kong V. Cheung, U.S. Appl. No. 12/036,462, filed Feb. 25, 2008.
U.S. Office Action, Dec. 17, 2008, for Nai-Kong V. Cheung, U.S. Appl. No. 10/565,484, filed Jan. 17, 2006.
U.S. Office Action, Jun. 16, 2009, for Nai-Kong V. Cheung, U.S. Appl. No. 10/565,484, filed Jan. 17, 2006.
U.S. Office Action, May 27, 2010, for Rolf Einar Egstad, U.S. Appl. No. 12/151,285, filed Jul. 17, 2008.
Hanaue, H., Y. Tokuda, T. Machimura, A. Kamijoh, Y. Kondo, K. Ogoshi, H. Makuuchi, H. Nakasaki, T. Tajima, and T. Mitomi. 1989. "Effects of oral lentinan on T-cell Subsets in Peripheral Venous Blood". Clin. Ther. 11:614-622.
Hayakawa, K., N. Mitsuhashi, Y. Saito, M. Takahashi, S. Katano, K. Shiojima, M. Furuta, and H. Niibe. 1993. "Effect of Krestin (PSK) as Adjuvant Treatment on the Prognosis after Radical Radiotherapy in Patients with Non-small Cell Lung Cancer". Anticancer Res. 13:1815-1820.
Hishida. I., H., Nanba, and H. Kuroda. 1988. "Antitumor Activity Exhibited by Orally Administeres Extract from Fruit Body by Grifola frondosa (Maitake)", Chem. Pharm. Bull (Tokyo) 36:1819-1827.
Hotta, H., K. Hagiwara, K. Tabata, W. Ito, and M. Homma. 1993. "Augmentation of protective immune responses against Sendai virus infection by fungal polysaccharide schizophyllan". Int. J. Immunopharmacol. 15:55-60.
Iino, Y., T. Yokoe, M. Maemura, J. Horiguchi, H. Takei, S. Ohwada, and Y. Morishita. 1995. "Immunochemotherapies verus Chemotherapy as Adjuvant Treatment after Curative Resection of Operable Breast Cancer". Anticancer Res. 15:2907-2912.
Michaelson et al., 1992, "Antibody dependent cell-mediated cytoxicity induced by chimeric mouse-human IgG subclasses and IgG3 antibodies with altered hinge region", Molecular Immunology, 29(3):319-326 (abstract only).

(56) References Cited

OTHER PUBLICATIONS

Morinaga, H., K. Tazawa, H. Tagoh, A. Muraguchi, and M. Fujimaki. 1994. "An in vivo study of hepatic and splenic interleukin-1β mRNA expression following oral PSK or LEM administration". Gann 85:1298-1303.
Nanba, H., K. Mori, T. Toyomasu, and H. Kuroda. 1987. "Antitumor action of shiitake (Lentinus edodes) fruit bodies orally administered to mice". Chem. Pharm. Bull. (Tokyo) 35:2453-2458.
Nanba, H. 1995. "Activity of Maitake D-faction to Inhibit Carcinogensis and Metastasis". Ann. N.Y. Acad. Sci. 768:243-245.
Nanba, H. and H. Kuroda. 1987. "Antitumor Mechanisms of Orally Administered Shiitake Fruit Bodies". Chem. Pharm. Bull. (Tokyo) 35:2459-2464.
Nanba, H. and H. Kuroda. 1988. "Potentiation of Host-Mediated Antitumor Activity by Orally Administered Mushroom (Agaricus bispora) Fruit Bodies". Chem. Pharm. Bull. (Tokyo) 36:1437-1444.
Ohmori, T., K. Tamura, A. Wakaiki, G. Kawanishi, S. Tsuru, T. Yadomae and K. Nomoto. 1988. "Dissociation of a Glucan Fraction (CO-1) from Protein-bound Polysaccharide of Cordyceps ophioglossides and Analysis of its Antitumor Effect". Chem. Pharm. Bull. (Tokyo) 36:4512-4518.
Ostroff et al., "Immune-Enhancing Effects of Oral Yeast β 1,3/1,6 Glucans", American Chemical Society, vol. 225, No. 1-2, pp. AGFD 8 (2003).
Ross, et al., "Therapeutic intervention with complement and β-glucan in cancer", Immunopharmacology 42(1999), 61-74.
Sakurai, T., K. Hashimoto, I. Suzuki, N. Ohno, S. Oikawa, A. Masuda, and T. Yadomae. 1992. "Enhancement of Murine Alveolar Macrophage Functions by Orally Administered β-glucan". Int. J. Immunopharmacol. 14:821-830.
Shimazu, H. et al., "Intravenous chronic toxicity of lentinan in rats: 6-month treatment and 3-month recovery (author transl.)", National Library of Medicine (PubMed), J Toxicol Sci., pp. 33-57 (1980).
Sortwell, R. et al., "Chronic Intravenous Administration of Lentinan to the Rhesus Monkey", Toxicology Letters, vol. 9, pp. 81-85 (1981).
Suzuki, et al., "Effect of orally administered β-glucan on macrophage function in mice". Int. J. Immunopharmacology 12:6, 675-684, 1990.
Suzuki, M. et al., "Antitumor and Immunological Activity of Lentinan in Comparison with LPS", International Society for Immunopharmacology, pp. 463-468(1994).
Suzuki, I., K. Hashimoto, N. Ohno, H. Tanaka, and T. Yadomae. 1989. "Immunomodulation by Orally Administered β-glucan in Mice". Int. J. Immunopharmacol. 11:761-769.
Suzuki, I., T. Sakurai, K. Hashimoto, S. Oikawa, A. Masuda, M. Ohsawa, and T. Yadomae. 1991. "Inhibition of Experimental Pulmonary Metastasis of Lewis Lung Carcinoma by Orally Administered β-glucan in Mice". Chem. Pharm. Bull. (Tokyo) 39:1606-1608.
Tsukagoshi, S., Y. Hashimoto, G. Fujii, H. Kobayashi, K. Nomoto, and K. Orita. 1984. "Krestin (PSK)", Cancer Treat. Rev. 11:131-155.
Urbaniak, S. J. and Greiss M. A., 1980, "ADCC (K-cell) lysis of human erythrocytes sensitized with rhesus alloantibodies. III. Comparison of IgG anti-D agglutinating and lytic (ADCC) activity and the role of IgG subclasses", British Journal of Hematology, 46(3):447-453 (abstract only).
Vetvicka, et al. "Pilot Study: Orally-administered Yeast Beta 1,3-glucan Prophylactically protects against anthrax infection and cancer in mice". Journ. Amen. Nutraceutical Assoc., vol. 5:2, Apr. 22, 2002.
Vetvicka, V., B.P. Thornton and G.D. Ross, "Soluble β-Glucan Polysaccharide Binding to the Lectin Site of Neutrophil or Natural Killer Cell Complement Receptor Type3 (CD11b/CD18) Generates a Primed State of the Receptor Capable of Mediating Cytotoxicity of iC3b-Opsonized Target Cells". J. Clin. Invest., 98:50-61, 1996.
Xia, Y., V. Vetvicka, J. Yan, Ni. Hanikyrova, T. Mayadas and G.D. Ross, "The β-Glucan-Binding Lectin Site of Mouse CR3 (CD11b/CD18) and Its Function in Generating a Primed State of the Receptor That Mediates Cytotoxic Activation in Response to iC3b-Opsonized Target Cells". J. Immunology, 162:2281-2290, 1999.
Yan, J. et al., "β-Glucan, a "Specific" Biologic Response Modifier That Uses Antibodies to Target Tumors for Cytotoxic Recognition by Leukocyte Complement receptor Type 3 (CD11b/CD18)". The Journal of Immunology, 163:3045-3052, 1999.
Canadian Office Action, Jan. 27, 2012, for Sloan-Kettering Institute for Cancer Research, Canadian Application No. 2,637,205, Filed Oct. 28, 2008, National Stage of PCT/US07/001427, Filed Jan. 17, 2007.
Chinese Office Action, Nov. 2, 2011, for Sloan-Kettering Institute for Cancer Research, Chinese Application No. 2007800075400, Filed Sep. 2, 2008, National Stage of Int'l App'l No. PCT/US07/01427, Filed Jan. 17, 2007.
European Office Action, May 3, 2012, for Sloan-Kettering Institute for Cancer Research, European Application No. 07 71 8218, National Stage of PCT/US04/23099, Filed Jul. 16, 2004.
European Office Action, Apr. 5, 2012, for Sloan-Kettering Institute for Cancer Research, European Application No. 04 78 6081, Filed Jul. 16, 2008, National Stage of PCT/US07/01427, Filed Jan. 17, 2007.
European Office Action, Aug. 17, 2012, for Sloan-Kettering Institute for Cancer Research, European Application No. 02 707 502.7, National Stage of PCT/US02/01276, Filed Jan. 15, 2002.
Japanese Office Action, Aug. 26, 2011, for Sloan-Kettering Institute for Cancer Research, Japanese Application No. 2006-520398, Filed Jan. 16, 2006, National Stage of Int'l App'l No. PCT/US04/23099, Filed Jul. 16, 2004.
Japanese Office Action, May 6, 2011, for Sloan-Kettering Institute for Cancer Research, Japanese Application No. 2006-520398, Filed Jan. 16, 2006, National Stage of Int'l App'l No. PCT/US04/23099, Filed Jul. 16, 2004.
Japanese Office Action, Jul. 13, 2012, for Sloan-Kettering Institute for Cancer Research, Japanese Application No. 2008-551413, Filed Jul. 16, 2008, National stage of Int'l App'l No. PCT/US07/01427, Filed Jan. 17, 2007.
Korean Office Action, Apr. 12, 2011, for Sloan-Kettering Institute for Cancer Research, Korean Application No. 10-2006-7000839, Filed Jan. 13, 2006, National Stage of Int'l App'l No. PCT/US04/23099, Filed Jul. 16, 2004.
U.S. Office Action, Sep. 27, 2011, for Rolf Einar Engstad, U.S. Appl. No. 12/161,285, filed Jul. 17, 2008.
U.S. Office Action, Sep. 27, 2011, for Nai-Kong V. Cheung and Rolf Einar Engstad, U.S. Appl. No. 12/212,352, filed Sep. 17, 2008.
U.S. Office Action, Mar. 13, 2012, for Rolf Einar Engstad and Nai-Kong V. Cheung, U.S. Appl. No. 12/161,285, filed Jul. 17, 2008.
U.S. Office Action, Mar. 7, 2012, for Nai-Kong V. Cheung and Rolf Einar Engstad, U.S. Appl. No. 12/212,352, filed Sep. 17, 2008.
U.S. Office Action, Jul. 27, 2012, for Nai-Kong V. Cheung, U.S. Appl. No. 12/212,352, filed Sep. 17, 2008.
U.S. Office Action, Jul. 18, 2012, for Nai-Kong V. Cheung, U.S. Appl. No. 12/814,174, filed Jun. 11, 2010.
U.S. Office Action, May 29, 2012, for Nai-Kong V. Cheung, U.S. Appl. No. 12/767,237, filed Apr. 26, 2012.
U.S. Office Action, May 22, 2012, for Nai-Kong V. Cheung, U.S. Appl. No. 12/854,603, filed Aug. 11, 2010.
U.S. Office Action, Nov. 6, 2012, for Nai-Kong V. Cheung, U.S. Appl. No. 12/767,237, filed Apr. 26, 2012.
U.S. Office Action, Nov. 9, 2012, for Nai-Kong V. Cheung, U.S. Appl. No. 12/854,603, filed Aug. 11, 2010.
U.S. Office Action, Dec. 10, 2012, for Nai-Kong V. Cheung, U.S. Appl. No. 12/814,174, filed Jun. 11, 2010.
U.S. Office Action, Feb. 22, 2013, for Nai-Kong V. Cheung, U.S. Appl. No. 12/814,174, filed Jun. 11, 2010.
U.S. Office Action, Mar. 21, 2013, for Nai-Kong V. Cheung, U.S. Appl. No. 12/814,174, filed Jun. 11, 2010.
U.S. Office Action, Jun. 18, 2013, for Nai-Kong V. Cheung, U.S. Appl. No. 12/854,603, filed Aug. 11, 2010.
U.S. Office Action, Feb. 28, 2014, for Nai-Kong V. Cheung, U.S. Appl. No. 13/859,096, filed Apr. 9, 2013.
U.S. Office Action, Dec. 13, 2013, for Nai-Kong V. Cheung, U.S. Appl. No. 13/859,096, filed Apr. 9, 2013.
U.S. Office Action, Jul. 15, 2013, for Nai-Kong V. Cheung, U.S. Appl. No. 13/859,096, filed Apr. 9, 2013.
Ara et al., 2001, "Zymosan enhances the immune response to DNA vaccine for human immunodeficiency virus type-1 through the activation of complement system", Immunology, 103: 98-105.

(56) References Cited

OTHER PUBLICATIONS

Gawronski et al., 1999, "Microfibrillar Structure of PCG-Glucan in Aqueous Solution as Triple-Helix Aggregates by Small Angle X-Ray Scattering", Biopolymers, 50: 569-578.
Hazama et al., 2009, "Efficacy of Orally Administered Superfine Dispersed Lentinan (β-1,3-Glucan) for the Treatment of Advanced Colorectal Cancer", Anticancer Research, 29: 2611-2618.
Hsu, Frank and Komarovskaya, Marina, 2002, "CTLA4 Blockade Maximizes Antitumor T-Cell Activation by Dendritic Cells Presenting Idiotype Protein or Opsonized Anti-CD20 Antibody-Coated Lymphoma Cells", Journal of Immunology, 25(6): 455-468.
Onrust et al., 1999, "Rituximab", Drugs, 58(1):79-88 (abstract only).
European Office Action, Jun. 3, 2014, for Sloan-Kettering Institute for Cancer Research, European Application No. 07 71 8218, National Stage of PCT/US04/23099, Filed Jul. 16, 2004.
Adachi et al., 1990, "Macrophage Activation in Vitro by Chemically Cross-Linked (1-3)-β-D-Glucans", Chem. Pharm. Bull., 38(4):988-992.
Allendorf et al., "Macrophages shuttle orally administered β-glucan to potentiate the CR3-dependent tumoricidal effects of monoclonal antibodies in mouse tumor models", FASEB Journal, vol. 17, No. 7, p. C128 (2004).
"Allendorf et al., 2005, ""C5a-Mediated Leukotriene B4-Amplified Neutrophil Chemotaxis Is Essential in Tumor Immunotherapy Facilitated by Anti-Tumor Monoclonal Antibody and β-GJucan"", Journal of Immunology,174:7050-7056.".
Andoh, T., 1992, "Effects of Pervenous Administration of Lentinan and Concomitant Perendoscopic Localized Injection on Gastric Carcinoma in Elderly Patients", Nichidai Igaku Zasshi, 51(6):587-596. (abstract only).
Arturson, G. et al, "Intravascular Persistence and Renal Clearance of Dextran of Different Molecular Sizes in Normal Children", Arch. Dis. Childh., vol. 41, pp. 168-172 (1966).
Azuma, Ichiro, "Development of Immunostimulants in Japan", Immunostimulants: Now and Tomorrow, 41-56.
Babineau, T. et al., "A Phase II Multicenter, Double-blind, Randomized, Placebo-Controlled Study 01 Three Dosages of an Immunomodulator (PGG-Glucan) in High-Risk Surgical Patients", Arch. Surg., vol. 129. pp. 1204-1210(1994).
Babineau, T. et al., "Randomized Phase I/II Trial of a Macrophage-Specific Immunomodulator(PGG-Glucan) in High-Risk Surgical Patients", Annals of Surgery, vol. 220, No. 5, pp. 601-609(1994).
Basic and Clinical Pharmacology, 7th edition 1998, Bertram G. Katzung, pp. 881-884.
Bergman et al., 1999, "Treatment of Neoplastic Meningeal Xenografts by Intraventricular Administration of an Antiganglioside Monoclonal Antibody, 3F8." Int. J. Cancer, 82:538-548.
Bluhm et al.. 1977, "The triple helical structure of lentinan, a linear-(1→3)-β-glucan", Can J Chem, 55:293-299.
Bogwald et al., 1982, "The Cytoxic Effect of Mouse Macrophages Stimulated in Vitro by a β-1 ,3-D-Glucan from Yeast Cell Walls", Scandinavian Journal of Immunology, 15:297-304.
Bohn, J.A., and BeMiller, J,N., 1995, "(1 → 3)-β-Glucans as biological response modifiers: a review of structure-functional activity relationships," Carbohydrate Polymers, 28:3-14.
Bowers et al., 1989, "Gluean Enhances Survival in an Intraabdominal Infection Model", Journal of Surgical Research, vol. 47(2):183-188.
Capurro et al., 1998, "FC-2.15, a monoclonal antibody active against human breast cancer, specifically recognizes Lewisx hapten," Cancer Immunol. Immunother., 45:334-339.
Chan et al., 2007, "Response of human dendritic cells to different immunomodulatory polysaccharides derived from mushroom and barley", International Immunology, 19(7):891-899.
"Cheung et al., 2006, ""FCGR2A Polymorphism Is Correlated With Clinical Outcome After Immunotherapy of Neuroblastoma With Anti-GD2 Antibody and Granulocyte Macrophage Colony-Stimulating Factor"", Journal ClinicalOncology, 24(18):2885-2890".
Cheung et al., 1994, "Antibody Response to Murine Anti-GD2 Monoclonal Antibodies:Correlation with Patient Survival", Cancer Research, 54(8):2228-2233.

Cheung, N.-K. V., et al., 2002, "Quantitation of GD2 Synthase mRNA by Real-Time Reverse Transcription-Polymerase Chain Reaction—Utility in Bone Marrow Purging of Neuroblastoma by Anti-G02 Antibody 3F8," Cancer, 94:3042-3048.
Cheung, N.-K. V., et al., Jun. 1985, "Monoclonal Antibodies to a Glycolipid Antigen on Human Neuroblastoma Cells," Canc. Res., 45:2642-2649.
Chihara et al., 1970, "Fractionation and purification of the polysaccharides with Marked Antitumor Activity, Especially Lentinan, from Lentinus edodes (Berk.) Sing. (an Edible Mushroom)", Cancer Res, 30:2776-2781.
Chihara et al., 1981, "The antitumor polysaccharide Lentinan: an overview", Manipulation of Host Defence Mechanisms, 1-16.
Chihara et al. , 1982, "Current Status and Perspectives of Immunomodulators of Microbial Origin", International Journal of Tissue Reactions, 4:207-225.
Chihara, G. et al., "Antitumor and Metastasis-Inhibitory Activities of Lentinan as an Immunomodulator: An Overview", Cancer Detection and Prevention Supplement vol. 1, pp. 423-443(1987).
Damge et al., Dec. 1996, "Intestinal absorption of PLAGA microspheres in the rat," J. Anat., 189:491-501.
D'Amico et al., 2000, "Molecular Biologic Substaging of Stage I Lung Cancer According to Gender and Histology," Ann. Thorac. Surg 69:882-886.
David at al., 1996, "Growth arrest of solid human neuroblastoma xenografts in nude rats by natural IgM from healthy humans," Nature Medicine, 2:686-689.
Dellinger, E., et al., "Effect of PGG-glucan on the Rate of Serious Postoperative Infection or Death Observed After High Risk Gastrointestinal Operations", Arch. Surg., vol. 134, pp. 977-983(1999).
Dhodapkar et al., 2002, "Antitumor Monoclonal Antibodies Enhance Cross-Presentation of Cellular Antigens and the Generation of Myeloma-specific Killer T Cells by Dendritic Cells", Journal Experimental Medicine, 195(1): 125-133.
Di Luzio et al., 1980, "Comparative Evaluation of the Tumor Inhibitory and Antibacterial Activity of Solubilized and Particulate Glucan", Recent Results in Cancer Research, 75:165-172.
Di Luzio et al., 1985, "Glucans as Immunomodulators", Advances in Immunophamnacology, Permagon Press, NY, 369-375.
Di Luzio, Nicholas R, 2003, "Immunopharmacology of glucan: a broad spectrum enhancer of host defense mechanisms", T.I.P.S., 344-347.
Di Luzio, Nicholas R., 1985, "Update on the Immunomodulating Activities of Glucans", Springer Seminars in Immunopathology, 8:387-400.
Diaz De Stahl et al., 2003, "A role for complement ',n feedback enhancement of antibody responses by IgG3", Journal Experimental Medicine, 197(9): 1183-1190.
Diller et al., 1963, "The effect of Yeast Polysaccharides on Mouse Tumors", Cancer Research, 23:201-211.
Dillman et al., 2001, "Monoclonal antibodies in the treatment of malignancy: Basic concepts and recent developments", Cancer Investigation, 19(8):833-841.
"Engler et al., Apr. 1 , 2001, ""A Novel Metastatic Animal Model Reflecting the Clinical Appearance of Human Neuroblastoma: Growth Arrest of Orthotopic Tumors by Natural, Cytotoxic Human Immunoglobulin M Antibodies,""Cancer Research 61:2968-2973".
Engstad et al., 2002, "The effect of soluble beta-1 ,3-glucan and lipopolysaccharide on cytokine production and coagulation activation in whole blood", International Immunopharmacology, 2(11):1585-1597 (abstract only).
Florence A., 1997, "The oral absorption of micro- and nanoparticulates: Neither exceptional nor unusual," Pharmaceutical Research, 14(3):259-266.
Furue et al., 1985, "Clinical evaluation of schizophyllan (SPG)in advanced gastric cancer (the second report): a randomized controlled study," Gan to Kagaku Ryoho, 12: 1272-1277.
Gelderman et al., 2004, "Complement function in mAb-mediated cancer immunotherapy", Trends in Immunology, 25(3):158-164.
Hamuro et al., 1978, "Solid phase activation of alternative pathway of complement by β-1 ,3-glucans and its possible role for tumour regressing activity", Immunology, 34:695-705.

(56) References Cited

OTHER PUBLICATIONS

Hamuro et al., 1971, "The significance of the higher structure of the polysaccharides lentinan and pachymaran with regard to their antitumour activity", Chem. Biol. Interactions, 3:69-71.

Hamuro, Junji, 2005, "Anticancer immunotherapy with perorally effective Lentinan", Cancer & Chemotherapy, 32 (8): 1209-1215. (abstract only).

Harada et al., 1997, "Oral Administration of PSK can Improve the Impaired Anti-Tumor CD4+ T-Cell Response in Gut-Associated Lymphoid Tissue (GALT) of Specific-Pathogen-Free Mice," Int. J. Cancer, 70:362-372.

Hellstrom, I. et al., Sep. 1986, "Antitumor effects of L6, and IgG2a antibody that reacts with most human carcinomas," Proc. Natl. Acad. Sci. USA, 83:7059-7063.

Herlyn et al., 1985, Stimulation of monocloni antibody-dependent macrophage-mediated cytotoxicity against human tumors by lentinan, International Journal of Immunopharmacology, 7(3):332. (abstract only).

Herre et al., Feb. 2004, "Dectin-1 and its role in the recognition of β-glucans by macrophages," Mol. Immunol. 40(12):869-876.

Herrera et al., 2000, "Immunotoxins against CD19 and CD22 are effective in killing precursor-B acute lymphoblastic leukemia cells in vitro," Leukemia, 14:853-858.

Hiroaki Nanba and Keiko Kubo, 1997, "Effect of Maitake D-Fraction on Cancer Prevention," Annal. N.Y. Acad. Sci. 833:204-207.

Hong et al., 2003, "β-Glucan Functions as an Adjuvant for Monoclonal Antibody Immunotherapy by Recruiting Tumoricidal Granulocytes as Killer Cells", Cancer Research, 63(24):9023-9031.

Hong et al., "Mechanism by Which Orally Administered β-1,3-Glucans Enhance the Tumoricidal Activity of Antitumor monoclonal Antibodies in Murine Tumor Models", The Journal of Immunology, vol. 173, No. 5, pp. 797-806 (2004).

Iannello et al., 2005, "Role of antibody-dependent cell-mediated cytotoxicity in the efficacy of therapeutic anti-cancer monoclonal antibodies", Cancer Metastasis, 24(4):487-499.

Imai et al., 2005, "Complement-Mediated Mechanisms in Anti-GD2 Monoclonal Antibody Therapy of Murine Metastatic Cancer", Cancer Research, 65(22):10562-10568.

Jamas et al., 1990, "Spectral Analysis of Glucan Produced by Wild-Type and Mutant *Saccharomyces cerevisiae*", Carbohydrate Polymers, 13:207-219.

Jani et al., Dec. 1990, "Nanoparticle uptake by the rat gastrointestinal mucosa: quantitation and particle size dependency," J. Pharm. Pharmacol., 42:821-826.

Kaneko et al., 1989, Activity of Lentinan against Cancer and AIDS, International Journal of Immunotherapy, 5(4):203-213.

"Kernodle et al., Mar. 1998, ""Prophylactic Anti-Infective Activity of Poly-[1-6]-β-D-Glucopyranosyl [1-3]-βD-Glucopyranose Glucan in a Guinea Pig Model of Staphylococcal Wound Infection,"" Antimicrobial Agents andChemotherapy, 42(3):545-549".

Kidd, P., "The Use of Mushroom Glucans and Proteoglycans in Cancer Treatment", Alternative Medicine Review, vol. 5, No. 1, pp. 4-27(2000).

"Kim, Y.-S., et al., Oct. 20, 2000, ""Gram-negative Bacteria-binding Protein, a Pattern Recognition Receptor for Lipopolysaccharide and β-1, 3-Glucan That Mediates the Signaling for the Induction of Innate Immune Genes in*Drosophila melanogaster* Cells,"" J. Biol. Chem., 275(42):32721-32727".

Kirby et al, 1981, "Oat-bran intake selectively lowers serum low-density lipoprotein cholesterol concentrations of hypercholesterolemic men", American Journal of Clinical Nutrition, 34:824-829.

Komatsu et al., 1975, "Influence of Schizophyllan, Streptomycin and Rifampicin on Histopathological changes in mice infected with Tubercle Bacilli", Japanese Journal of Antibiotics, XXVII(4):549-557. (English abstract included).

Kotera, Y., et al, Jun. 1, 1994, "Humoral Immunity against a Tandem Repeat Epitope of Human Mucin MUC-1 in Sera from breast, Pancreatic, and Colon Cancer patients," Cancer Res., 54:2856-2860.

Kushner et al., 2001, "Phase II Trial of the Anti-GD2 Monoclonal Antibody 3F8 and Granulocyte-Macriphage Colony-Stimulating Factor for Neuroblastoma", Journal Clinical Oncology, 19(22):4189-94.

"Lehne et al., 2005, ""Oral administration of a new soluble branched β-1, 3-D-glucan is well tolerated and can lead to increased salivary concentrationsl of immunoglobulin A in healty volunteers""", Clinical and Experimental Immunology,143:65-69".

Li et al., 2007, "Combined Yeast β-Glucan and Antitumor Moloclonal Antibody Therapy Requires C5a-Mediated D Neutrophil Chemotaxis via Regulation of Decay-Accelerating Factor CD55", Cancer Research, 67:7421-7430.

Maeda et al., 1971, "Lentinan, a new immune-accelerator of cell-mediated responses", Nature, 229-634.

Maloney et al., Sep. 15, 1997, "IDEC-C2B8 (Rituximab) Anti-CD20 Monoclonal Antibody Therapy in Patients With Relapsed Low-Grade Non-Hodgkin's Lymphoma," Blood, 90(6):2188-2195.

Matzinger, P., 1994, "Tolerance, Danger, and the Extended Family," Annu. Rev. Immunol., 12:991-1045.

Mayell M, Feb. 2001, "Maitake Extracts and Their Therapeutic Potential—A Review," Altern. Med, Rev., 6(1):48-60.

Mehvar, R., "Recent Trends in the Use of Polysaccharides for Improved Delivery of Therapeutic Agents: Pharmacokinetic and Pharmacodynamic Perspectives", Current Pharmaceutical Biotechnology, vol. 4, pp. 283-302 (2003).

Mendelsohn et al., 1988, "Monoclonal Antibodies Against the Receptor for Epidermal Growth Factor as Potential Anticancer Agents," Cellular and Molecular Biology of Tumors and Potential Clinical Applications, 307-312.

Mendelsohn, J., Dec. 1997, "Epidermal Growth Factor Receptor Inhibition by a Monoclonal Antibody as Anticancer Therapy," Clin. Cancer Res., 3:2703-2707.

Nakao et al., 1983, "Clinical evaluation of schizophyllan (SPG) in advanced gastric cancer—a randomized comparative study by an envelope method," Gan To Kagaku Ryoho, 10: 1146-1159.

Nakazato et al., 1994, "Efficacy of immunotherapy as adjuvant treatment after curative resection of gastric cancer," The Lancet, 343:1122-1126.

Nicolosi et al., 1999, "Plasma lipid changes after supplementation with β-glucan fiber from yeast," Am. J. Clin. Nutr., 70:208-212.

Ohno et al., 2000, "Antitumor 1,3-β-Glucan from Cultured Fruit Body of Sparassis crispa," Biol. Pharm. Bull.,23(7):866-872.

Ollert et al., Apr. 1996, "Normal human serum contains a natural IgM antibody cytotoxic for human neuroblastoma ceils," Proc. Natl. Acad. Sci. USA, 93:4498-4503.

Ollert et al., Oct. 1997, "Mechanisms of in vivo antineuroblastoma activity of human natural IgM," European Journal of Cancer, 33(12): 1942-1948.

Onizuka et al., Jul. 1, 1999, "Tumor Rejected by in Vivo Administration of Anti-CD25 (Interleukin-2 Receptor α) Monoclonal Antibody," Cancer Research, 59:3128-3133.

Papila et al., "The Effect of Oral β-glucan in Addition to Systemic Chemotherapy on the Leukocyte Values and Oral mucositis in the Patients with Head-neck Tumors", International Review of Allergology & Clinical Immunology, vol. 10, No. 2, pp. 59-61 (2004).

Patchen et al., 1984, ~Soluble Polyglycans Enhance Recovery from Cobalt-60-Induced Hemopoietic Injury, Journal of Biological Response Modifiers, 3:627-633.

Peat et al., 1959, "Polysaccharides of Baker's Yeast. Part II. Yeast Glucan", Journal Chem. Soc. Part 1,3862-3868.

Rai, K.R. and Gupta, N., Jun. 2000, "Monoclonal Antibodies in Chronic Lymphocytic Leukemia," Rev. Clin. Exp. Hematol.,4.2:134-144.

Ren et al., 1997, "Mechanisms of Anti-Lung Cancer Activity for Monoclonal Antibody to Epidermal Growth Factor Receptor," Disi Junyi Daxue Xuebao, 18(6):560-562 (abstract only).

Robbins et al., 1977, "Cholesterol Lowering Effect of Dietary Yeast and Yeast Fractions", Journal of Food Science, 42 (3):694-698.

"Saito et al., 1977, ""A C-N.M.R.-spectral study of a gel fomning, branched (1→3)-β-D-Glucan, (Lentinan) from Lentinus edodes, and its acid-degraded fractions. Structure, and Dependence of Confirmation on the Molecular Weight"",Carbohydrate Research, 58:293-305".

(56) References Cited

OTHER PUBLICATIONS

Sano et al., 2002, "Antitumor Effects Induced by the Combination of TNP-470 as an Angiogenesis Inhibitor and Lentinan as a Biological Response Modifier in a Rabbit Spontaneous Liver Metastasis Model", Surgery Today 32:503-509.

Sasaki et al., 1976, "Antitumor Activity of Degraded Products of Lentinan: it's Correlation with Molecular Weight", Gann, 67:191-195.

Seljelid et al 1977, "Glycan Stimulation of Macrophages in Vitro", Experimental Cell Research, 131:121-129.

Seljelid et al., 1986, "A water soluble aminated β-1,3-D-glucose derivative caused regression of solid tumors in mice", Bioscience Reports 6:845-852.

Shiio et al., 1977, "A study of the condition of additive use of immunotherapeutic agent, Lentinan, and chemotherapeutic agent, Cyclophosphamide", Journal of Japan Society for Cancer Therapy, 15:436. (abstract only).

Singh et al., 1974, "Scleroglucan, an antitumor polysaccharide from Sclerotium glucanicum", Carbohydrate Research, 37:245-247.

Slovin. S.F. et. al., May 1999, "Carbohydrate vaccines in cancer: Immunogenicity of a fully synthetic globo H hexasaccharide conjugate in man," Proc. Natl. Acad. Sci. USA, 96:5710-5715.

Soiffer et al., 1997, "Administration of R24 Monoclonal Antibody and Low-Dose Interleukin 2 for Malignant Melanoma," Clinical Cancer Research, 3:17-24.

Song et al, "Yeast gJucan and immunotherapy of infectious diseases", Yeast glucan and immunotherapy, chapter 18, 533-545.

Takita et al., 1998. "Successful treatment of hepatic metastasis of gastric cancer with 5'-DFUR and Lentinan", Cancer & Chemotherapy, 25(1):129-133. (abstract only).

"Torisu et al., 1990, ""Significant prolongation of disease-free period gained by oral polysaccharide K (PSK)48 administration after curative surgical operation of colorectal cancer,"" Cancer Immunology Immunotherapy, 31 (5):261-268".

Williams et al., 1991, "Development, physicochemical characterization and preclinical efficacy evaluation of a water soluble glucan sulfate derived from *Saccharomyces cerevisiae*," Immunopharmacology 22:139-155.

Yan et al., 2005, "Yeast whole glucan particle β-glucan in conjunction with antitumor monoclonal antibodies to treat cancer", Expert Opinion on Biological Therapy, 5(5):691-702.

Yoshitomi et al., 2005, "A role for fungal β-glucans and their Dectin-1 in the induction of autoimmune arthritis in genetically susceptible mice", Journal of Experimental Medicine, 201 (6):949-960.

Zhang et al., 1998, "Antibodies against CD2 Ganglioside Can Eradicate Syngeneic Cancer Micrometastases", Cancer Research, 58(13):2844-2849.

Zimmerman, J.W., et al., Aug. 21, 1998, "A Novel Carbohydrate-Glycosphingolipid Interaction between a β-(1-3)-Glucan Immunomodulator, PGG-glucan, and Lactosyceramide of Human Leukocytes," J. Biol. Chem., 273 (34):22014-22020.

\* cited by examiner

1A

R ANTERIOR L    L POSTERIOR R

1B

R ANT L    L POST R

Days from first treatment

Glucan versus no glucan

Glucan versus no glucan

THERAPY-ENHANCING GLUCAN

This application is a Continuation Application of U.S. Ser. No. 12/767,237, Filed Apr. 26, 2010, which is a continuation application of U.S. Ser. No. 10/565,484, Filed Jan. 17, 2006, which is a National Stage of International Application No. PCT/US2004/023099, Filed Jul. 16, 2004, which is a Continuation-In-Part of U.S. Ser. No. 10/621,027, Filed Jul. 16, 2003. The entire contents of the preceding applications are hereby incorporated by reference into this application.

Throughout this application, various references are cited. Disclosures of these publications in their entireties are hereby incorporated by reference into this application to more fully describe the state of the art to which this invention pertains.

BACKGROUND OF THE INVENTION

This disclosure relates to a method for introducing substances into cells comprising contacting a composition comprising orally administered beta-glucan with said cells. A feature of this invention provides a method for introducing substances into a subject comprising administering to the subject an effective amount of the above compositions. The substance which could be delivered orally includes but is not limited to peptides, proteins, RNAs, DNAs, chemotherapeutic agents, biologically active agents, and plasmids. Other small molecules and compounds may be used as well. Another feature of the present invention is a composition comprising orally administered beta-glucan capable of enhancing efficacy of IgM antibodies.

Glucans derived from cell walls of yeasts, such as *Saccharomyces cervisiae* or mutant yeast strains described in U.S. Pat. No. 5,250,436, the disclosure of which is incorporated herein in its entirety by reference, may be used in the above compositions. Glucans having β(1-3) and β(1-6) linkages may be prepared by the process described in U.S. Pat. Nos. 5,233,491 and 4,810,646, the disclosures of which are incorporated herein in their entirety by reference. Soluble or aqueous glucans which are suitable for oral administration may be produced by the process described in U.S. Pat. Nos. 4,810,646 and 5,519,009, the disclosures of which are incorporated herein in their entirety by reference.

Beta-glucans have been tested for tumor therapy in mice for nearly 40 years.[1,2] Several forms of mushroom derived beta-glucans are used clinically to treat cancer in Japan, including PSK (from *Coriolus versicolor*), Lentinan and Schizophyllan. In randomized trials in Japan, PSK has moderately, but significantly improved survival rates in some cancer trials: after gastrectomy,[3,4] colorectal surgery,[5,6] and esophagectomy[7] to remove primary tumors. Results have been less encouraging in breast cancer,[8,9] and leukemia.[10] Schizophyllan has improved survival of patients with operable gastric cancer,[11] inoperable gastric cancer,[12,13] and cervical cancer.[14] Again, though survival differences between groups were statistically significant, these improvements were modest. While beta-glucans are not widely used by Western oncologists, beta-glucan containing botanical medicines such as Reishi and maitake[15] are widely used by U.S. cancer patients as alternative/complementary cancer therapies. These previous studies that looked for a therapeutic effect of beta-glucan, did not incorporate co-administration of therapeutic monoclonal antibodies (MoAb) as part of the protocol. There is increasing evidence that antibody is necessary to deposit iC3b which acts as a potent opsonin of human tumors. When beta-glucan is administered without co-administration of MoAb, its tumor cytotoxic effect requires the presence of naturally-occurring antitumor antibodies which can be quite variable among patients and even in experimental mice.

Anti-tumor effect of beta-glucan when combined with cancer specific antibodies was previously described. Previous studies have shown that oral beta-glucans derived from barley or oats can greatly enhance the anti-tumor activity of anti-tumor monoclonal antibodies in xenograph models. See Therapy-Enhancing Glucan, Int'l Application No. PCT/US02/01276, filed Jan. 15, 2002. Cheung et al., Oral (1-3), (1-4)-beta-glucan synergizes with anti-ganglioside GD2 monoclonal antibody 3F8 in the therapy of neuroblastoma. Clin Cancer Res. 2002; 8:1217-1223. Cheung N K et al., Orally administered beta-glucans enhance anti-tumor effects of monoclonal antibodies. Cancer Immunol Immunother. 2002; 51:557-564. The phase I clinical trial supports the prediction that barley beta-glucan can enhance the antibody effect on metastatic cancer. As previously noted, lentinan and laminarin, both (1→3),(1→6)-β-D-glucans, were not as effective as barley glucan.[16] In addition, among the (1→3), (1→4)-β-D-glucans, small molecular weight preparations and Lichenans were not as effective. The molecular size and the fine structure of beta-glucan may have substantial influence on their synergistic effect on antibodies towards tumors.

In Europe and USA beta-glucans especially from Bakers' yeast have long been employed as feed additives for animals, as dietary supplement for humans,[17] in treatment of wounds, [18] and as an active ingredient in skin cream formulations. The basic structural unit in beta-glucans is the β(1→3)-linked glucosyl units. Depending upon the source and method of isolation, beta-glucans have various degrees of branching and of linkages in the side chains. The frequency and hinge-structure of side chains determines its immunomodulor effect. beta-glucans of fungal and yeast origin are normally insoluble in water, but can be made soluble either by acid hydrolysis or by derivatisation introducing charged groups like -phosphate, -sulphate, -amine, -carboxymethyl and so forth to the molecule.[19,20]

Soluble glucan with the molecular structure where (1→3)-β-D-glucan units form the backbone with branches made up of (1→3)-β-D-glucan units positioned at (1→6)-β-D-glucan hinges was isolated from Baker's yeast, *Saccharomyces cerevisiae*. High molecular weight fractions were obtained and

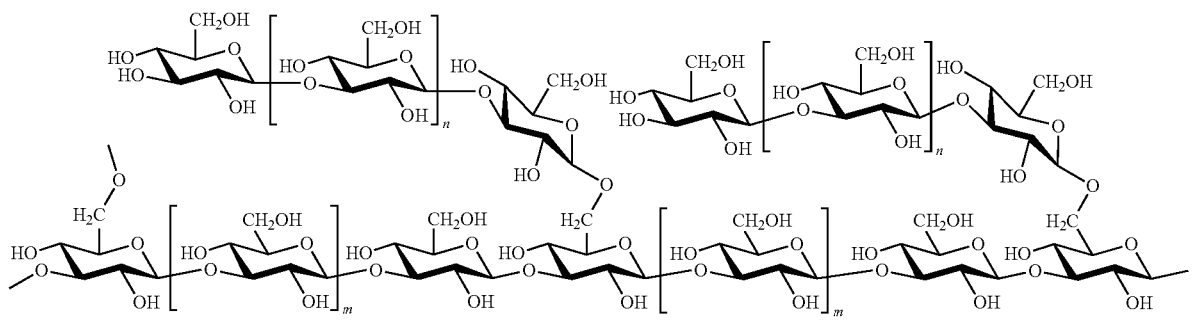

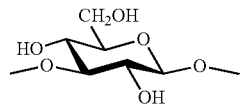

tested for synergy with monoclonal antibodies in tumor models. The anti-tumor effect of soluble yeast beta-glucan was found to be comparable to the anti-tumor effect of soluble barley beta-glucan, when combined with monoclonal antibodies specific for human cancer as detailed below.

SUMMARY OF THE INVENTION

This invention provides a method for introducing substances into cells comprising contacting a composition comprising orally administered beta-glucan with said cells.

Another aspect of the present is a method for introducing substances into a subject comprising administering to the subject an effective amount of the above compositions. The substance which could be delivered orally includes but is not limited to peptides, proteins, RNAs, DNAs, chemotherapeutic agents, biologically active agents, and plasmids. Other small molecules and compounds may be used as well.

A further aspect of the present invention is a composition comprising orally administered beta-glucan capable of enhancing efficacy of IgM antibodies.

DETAILED DESCRIPTION OF THE FIGURES

FIG. 1. Barley (1→3),(1→4)-β-D-glucan plus antibody in the treatment of metastatic neuroblastoma in patients. MIBG scan before and after treatment in a patient with metastatic neuroblastoma refractory to multiple regimens of chemotherapy. Patient received intravenous anti-GD2 antibody 3F8 (10 mg/m2/day) for a total of 10 days, plus oral barley beta-glucan over the same time period. FIG. 1A shows baseline MIBG scan of patient. Extensive osseous metastasis can be seen in the femora, fibulae, pelvis, ribs, left scapula, right clavicle, humeri, skull and spine. Heart, liver, stomach and colon uptakes are physiologic. FIG. 1B shows MIBG scan of same patient 2 months later, following a single cycle of therapy with 3F8 plus glucan. Areas of metastases have significantly improved.

FIG. 2. Barley (1→3),(1→4)-β-D-glucan plus antibody in treatment of subcutaneous human lymphoma xenografted in SCID mice. SCID mice with established subcutaneous Daudi (n=9) (FIG. 2A), Hs445 (n=5) (FIG. 2B), EBV-derived LCL (n=9) (FIG. 2C) and RPMI 6666 (n=10; data not shown) xenografts were treated either with 200 ug intravenous rituximab twice weekly for 8 doses (■), 400 ug (1→3), (1→4)-D-β-glucan administered orally via intragastric gavage daily for 29 days (Δ) or a combination of rituximab and (1→3), (1→4)-D-β-glucan (x), or left untreated (♦). Percentage tumor growth is plotted on y-axis and days after treatment was commenced on x-axis. Error bars represent SEM and have been shown only for rituximab alone and combination groups. For all xenografts, only combination treatment was associated with reduction in tumor growth. The reduction in tumor growth per day in the group receiving beta-glucan in addition to rituximab compared to rituximab alone was 2.0% (95% CI 1.3-2.7%; p<0.0005) for Daudi, 0.8% for EBV-derived LCL (95% CI 0.4-1.2%; p<=001), 2.2% for Hs445 (95% C.I. 1.2%-3.2%; p=0.0009), and 1.8% for RPMI6666 (95% CI 1.0-2.7%; p<0.0002; data not shown) xenografts.

FIG. 3. Barley (1→3),(1→4)-β-D-glucan plus antibody in treatment of disseminated human lymphoma xenografted in SCID mice. 5×10$^6$ Daudi (FIG. 3A) or Hs445 (FIG. 3B) cells in 100 µl normal saline were injected intravenously (IV) into SCID mice. Mice were treated either with 200 ug intravenous rituximab twice weekly for 8 doses ( - - - ), 400 ug (1→3), (1→4)-D-β-glucan administered orally via intragastric gavage daily for 29 days ( . . . ) or a combination of rituximab and (1→3), (1→4)-D-β-glucan (——), or left untreated (——) commencing 10 days after tumor implantation. Tumors grew systemically and mice became paralyzed when tumor cells infiltrated the spinal canal, resulting in hind-leg paralysis. Mice were sacrificed at onset of paralysis or when animals lost 10% of their body weight. Kaplan-Maier survival curves for the various groups are shown in FIGS. 2A (Daudi) and 2B (Hs445). Mice treated with a combination of (1→3), (1→4)-D-β-glucan and rituximab had a significantly increased survival when compared to all other treatment groups (p<0.0005 for Daudi and p=0.001 for Hs445) or when compared to rituximab alone (p<0.0005 for Daudi and p=0.01 for Hs445). Median survival for mice with no treatment, rituximab alone, BG, and rituximab+BG groups was 27, 71, 43 and 124 days respectively for Daudi xenografts, and 12, 16, 31 and 243 days respectively for Hs445 xenografts.

FIG. 4. Dose response of 3G6 (anti-GD2 IgM antibody) in the presence of barley β-glucan in the treatment of human neuroblastoma. Two million LAN1 neuroblastoma cells were xenografted subcutaneously in athymic Balb/c mice. Treatment started in groups of 5 mice each, 2 weeks after tumor implantation when visible tumors reached 0.7-0.8 cm diameter. 3G6 group (solid squares) was treated with 200 ug of intravenous 3G6 injected through the retroorbital plexus twice weekly (M and Th). 3G6+BG group was treated with 200 ug i.v. 3G6 twice weekly plus oral beta-glucan (BG) 400 ug daily by gavage for a total of 14-18 days. 3G6 was administered in 3 different doses (open triangle 8 ug per dose, open square 40 ug, open circle 200 ug). BG group (solid circles) received 400 ug oral beta-glucan alone. Tumor size was measured from the first day of treatment, and the product of the largest diameters expressed as percent of the size on day 0 of treatment. Vertical bars represent standard errors, depicted in only 4 groups for clarity. While BG alone and 3G6 alone showed no anti-tumor effect, the BG+200 ug 3G6 group showed highly significant tumor shrinkage and suppression which was 3G6 dose-dependent (p<0.05).

FIG. 5. Treatment of human neuroblastoma using 3G6 (anti-GD2 IgM antibody) in the presence of yeast (1→3), (1→6)-β-D-glucan. Two million LAN1 neuroblastoma cells were xenografted subcutaneously in athymic Balb/c mice. Treatment started in groups of 5 mice each, 2 weeks after tumor implantation when visible tumors reached 0.7-0.8 cm diameter. 3G6 group (solid squares) was treated with 200 ug of intravenous 3G6 injected through the retroorbital plexus twice weekly (M and Th) for a total of 5 doses. Particulate yeast glucan group (solid triangles) received 400 ug oral particulate yeast glucan alone. 3G6+whole yeast particles (open diamond) was treated with 200 ug iv 3G6 twice weekly plus yeast particles 400 ug daily by gavage for a total of 14-18 days. 3G6+soluble yeast glucan group was treated with 200 ug iv 3G6 twice weekly plus soluble yeast glucan 400 ug daily by gavage for a total of 14-18 days. 3G6+particulate yeast glucan group was treated with 200 ug i.v. 3G6 twice weekly plus particulate yeast glucan 400 ug daily by gavage for a total of 14-18 days. Tumor size was measured from the first day of treatment, and the product of the largest diameters expressed as percent of the size on day 0 of treatment. Vertical bars represent standard errors, depicted in only 4 groups for clarity. While glucan alone and 3G6 alone showed no anti-tumor effect, soluble and particulate yeast glucan when combined with 3G6 group showed highly significant tumor shrinkage and suppression ($p<0.05$).

FIG. 6. Treatment of human neuroblastoma using 3F8 (anti-GD2 IgG antibody) in the presence of barley and yeast β-glucan. Two million LAN1 neuroblastoma cells were xenografted subcutaneously in athymic Balb/c mice. Treatment started in groups of 5 mice each, 2 weeks after tumor implantation when visible tumors reached 0.7-0.8 cm diameter. 3F8 group (solid diamonds) was treated with 200 ug of intravenous 3F8 injected through the retroorbital plexus twice weekly (M and Th) for a total of 5 doses. Barley glucan group (solid squares) received 400 ug barely glucan alone. 3F8+ barley glucan group (open diamond) was treated with 200 ug i.v. 3F8 twice weekly plus barely glucan 400 ug daily by gavage for a total of 14-18 days. 3F8+ soluble yeast glucan group (open squares) was treated with 200 ug iv 3F8 twice weekly plus soluble yeast glucan 400 ug daily by gavage for a total of 14-18 days. Tumor size was measured from the first day of treatment, and the product of the largest diameters expressed as percent of the size on day 0 of treatment. Vertical bars represent standard errors. While glucan alone and 3F8 alone showed no anti-tumor effect, barley and soluble yeast glucan when combined with 3F8 group showed highly significant tumor shrinkage and suppression ($p<0.05$).

FIG. 7. Treatment of disseminating human lymphoma in SCID mice using Rituxan and barley or yeast β-glucan. 5×10e6 Daudi cells in 100 μl normal saline were injected intravenously (IV) into SCID mice. Tumors grew systemically and mice became paralyzed when tumor cells infiltrated the spinal canal, resulting in hind-leg paralysis. Mice were sacrificed at onset of paralysis or when animals lost 10% of their body weight. Therapy was initiated ten days after injection of tumor cells. 40 μg rituximab (Genentech, San Francisco, Calif.) was injected intravenously twice weekly for a total of eight injections and 400 μg glucan administered orally via intragastric gavage daily for 29 days. Mice were weighed weekly and observed clinically at least once daily. Mice receiving rituxan plus barley glucan or rituxan plus yeast soluble glucan have a highly significant prolonged survival ($p<0.05$).

DETAILED DESCRIPTION OF THE INVENTION

Figure 1:
Figure 1:
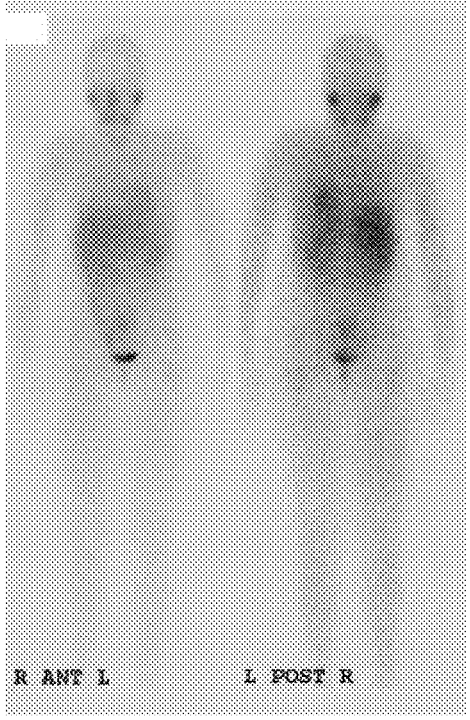

This invention provides a composition for oral uptake of substance comprising an appropriate amount of carbohydrates. In an embodiment, the carbohydrate is glucan.

When administered orally, glucan is taken up by macrophages and monocytes which carry these carbohydrates to the marrow and reticuloendothelial system from where they are released, in an appropriately processed form, onto myeloid cells including neutrophils, and onto lymphoid cells including natural killer (NK) cells. This processed glucan binds to CR3 on these neutrophils and NK cells, activating them in tumor cytotoxicity in the presence of tumor-specific antibodies.

Since macrophage and monocytes ingest glucan (whether soluble, gel or particle) from the gut, glucan is a potential conduit for gene therapy. Unlike proteins, DNA or plasmids are relatively heat-stable, and can be easily incorporated into warm soluble barley glucan which gels when cooled to room or body temperature. When mice are fed these DNA-glucan complexes, reporter genes can be detected in peripheral blood monocytes and macrophages within days. More importantly these reporter genes are expressed in these cells, a few days after ingestion of these DNA complexes. These findings have potential biologic implications. Glucan and similar carbohydrates may be conduits for DNA or plasmids to get into the human body. Oral glucan may be a convenient vehicle for correcting genetic defects of macrophages/monocytes, or administering genetic vaccines.

As it can easily be appreciated by an ordinary skilled artisan, other carbohydrates capable of functioning like glucan could be identified and used in a similar fashion. One easy screening for such carbohydrates can be established using glucan as the positive control.

The glucan includes but is not limited to β(1-3) and β(1-5) mixed linkage-glucan, and the glucan is of high molecular weight. The glucan may also have β(1-3) and β(1-6) linkages.

This invention also provides a method for introducing substance into cells comprising contacting the above compositions with said cells. One can use reporter genes or other markers to assess the efficiency of the said introduction. Reporter genes or markers are well known in the molecular biology field. In addition, this invention provides a method for introducing substance into a subject comprising administering to the subject an effective amount of the above compositions.

This invention provides a composition for the oral delivery of one or more substances comprising an effective amount of an orally administered beta-glucan and one or more chemotherapeutic agents.

In an embodiment, the glucan contains 1,3-1,6 or 1,3-1,4 mixed linkages, or a mixture of 1,3-1,6 and 1,3-1,4 mixed linkages. In another embodiment, the glucan enhances the efficacy of chemotherapeutic agents or anti-cancer antibodies.

In a further embodiment, the glucan is derived from grass, plants, mushroom, yeast, barley, fungi, wheat or seaweed. The glucan may be of high molecular weight. The molecular weight of the glucan may be at least 10,000 Daltons.

In a further embodiment, the substance is a peptide, protein, RNA, DNA, plasmid, or chemotherapeutic agent. As used herein, chemotherapeutic agents include chemicals that combat disease in the body of an animal or medications used to treat various forms of cancer.

This invention provides a method for introducing substance into cells comprising contacting the above-described composition with said cells.

The substance which could be delivered orally includes but is not limited to peptides, proteins, RNAs, DNAs, and plasmids. Other small molecules and compounds may be used as well.

This invention provides a method for treating a subject comprising administering to the subject an effective amount of the above composition. In an embodiment, the method further comprises the substance.

This invention provides a method for treating a subject with genetic disorder comprising administering to the subject an effective amount of the above-described composition and a substance capable of correcting said genetic disorder. The substance includes but is not limited to a peptide, protein, RNA, DNA, plasmid and other small molecule and compound.

This invention provides a composition comprising an effective amount of orally administered (1→3),(1→6) beta-glucan capable of enhancing efficacy of IgM antibodies.

This invention provides a composition comprising an effective amount of orally administered (1→3),(1→6) beta-glucan capable of enhancing efficacy of antibodies. Glucans derived from cell walls of yeasts, such as *Saccharomyces cervisiae* or mutant yeast strains described in U.S. Pat. No. 5,250,436, the disclosure of which is incorporated herein in its entirety by reference, may be used in the above compositions. Glucans having β(1-3) and β(1-6) linkages may be prepared by the process described in U.S. Pat. Nos. 5,233,491 and 4,810,646, the disclosures of which are incorporated herein in their entirety by reference. Soluble or aqueous glucans which are suitable for oral administration may be produced by the process described in U.S. Pat. Nos. 4,810,646 and 5,519,009, the disclosures of which are incorporated herein in their entirety by reference.

In an embodiment, the antibody is a monoclonal antibody, or an antibody against cancer or tumor cells, which include but are not limited to anti-CEA antibody, anti-CD20 antibodies, anti-CD25 antibodies, anti-CD22 antibodies, anti-HER2 antibodies, anti-tenascin antibodies, MoAb M195, Dacluzimab, anti-TAG-72 antibodies, R24, Herceptin, Rituximab, 528, IgG, IgM, IgA, C225, Epratuzumab, and MoAb 3F8. In another embodiment, the antibody is a tumor-binding antibody.

Moreover, the antibody is capable of activating complement and/or activating the antibody dependent cell-mediated cytotoxicity. In another embodiment, the antibody modulates T-cell or B-cell function.

In a further embodiment, the antibody is directed at the epidermal growth factor receptor, a ganglioside, such as GD3 or GD2.

In a further embodiment, the antibodies are effective against cancers which include neuroblastoma, melanoma, non-Hodgkin's lymphoma, Epstein-Barr related lymphoma, Hodgkin's lymphoma, retinoblastoma, small cell lung cancer, brain tumors, leukemia, epidermoid carcinoma, prostate cancer, renal cell carcinoma, transitional cell carcinoma, breast cancer, ovarian cancer, lung cancer, colon cancer, liver cancer, stomach cancer, or other gastrointestinal cancers.

In a further embodiment, the above-described composition is in a pharmaceutically acceptable carrier.

This invention provides a method for treating a subject comprising administrating the above-described composition to a subject.

This invention provides a composition comprising an effective amount of orally administered (1→3),(1→6) beta-glucan capable of enhancing efficacy of vaccines. In an embodiment, the vaccine is against cancer or infectious agents, such as bacteria, viruses, fungi, or parasites.

This invention provides a composition comprising an effective amount of orally administered (1→3),(1→6) beta-glucan capable of enhancing efficacy of natural antibodies or infectious agents.

This invention provides a composition comprising an effective amount of orally administered (1→3),(1→6) beta-glucan capable of enhancing host immunity.

This invention provides a composition comprising an effective amount of orally administered (1→3),(1→6) beta-glucan capable of enhancing the action of an agent in preventing tissue rejection. In an embodiment, the tissue is transplanted tissue or transplanted organ or the host as in graft-versus-host disease.

In an embodiment, the glucan of the above-described composition has high molecular weight. The molecular weight of glucan is at least 10,000 Daltons. In another embodiment, the glucan is derived from barley, oat, mushroom, seaweed, fungi, yeast, wheat or moss. In a further embodiment, the glucan is stable to heat treatment.

In a further embodiment, above-describe composition is stable after boiling for 3 hours. The effective dose of the above-described composition is about >=25 mg/kg/day, five days a week for a total of 2-4 weeks.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Example I

Phase I Study of Barley β-Glucan in Combination with Anti-GD2 Antibody in Stage 4 Neuroblastoma A total of 24 patients were studied. These patients are all children or adolescents with relapsed or refractory stage 4 neuroblastoma metastatic to bone, marrow or distant lymph nodes, some with large soft tissue masses. Beta-glucan was well tolerated with no dose-limiting toxicities. Anti-tumor responses were recorded for marrow disease (histology, MIBG scans), soft tissue tumors (CT), as well biochemical markers (urine VMA and HVA tumor markers). One example of tumor response is shown in FIGS. 1A and 1B: $^{131}$I-metaiodobenzylguanidine (MIBG) scans showing near-complete resolution of extensive metastases after one treatment cycle of 3F8 plus beta-glucan. These responses are uncommon in patients with refractory or relapsed metastatic stage 4 NB treated with 3F8 alone or 3F8 in combination with cytokines. The best response rate for 3F8 to date was in a Phase II trial of combination 3F8 plus GMCSF where 7 of 33 (21%) children achieved MIBG improvement. In contrast, 62% (13 of 21) evaluable patients on 3F8+beta-glucan had MIBG improvement, a near tripling of the response rate (p=0.008 by $\chi^2$). In addition, among 15 patients with marrow disease, 5 achieved complete marrow remission (30%), and 8 with stable disease in the marrow.
(See FIG. 1)

Example II

Rituximab activates complement-mediated and antibody-dependent cell-mediated cytotoxicities, and is effective against B-cell lymphomas. Beta-glucans are naturally occurring glucose polymers that bind to the lectin domain of CR3, a receptor widely expressed among leukocytes, priming it for binding to iC3b activated by antibodies. Barley-derived (1→3),(1→4)-β-D-glucan (BG), when administered orally (400 μg per day×29 days), strongly synergized with subtherapeutic doses of intravenous rituximab (200 μg twice/week×8 doses) in the therapy of CD20-positive human lymphomas. Growth of established subcutaneous non-Hodgkin's lymphoma (NHL) (Daudi and EBV-derived B-NHL) or Hodgkin's disease (Hs445 or RPMI6666) xenografted in SCID mice was significantly suppressed, when compared to mice treated with rituximab or BG alone. Survival of mice with disseminated lymphoma (Daudi and Hs445) was significantly increased. There was no weight loss or clinical toxicity in treated animals. This therapeutic efficacy and lack of toxicity of BG plus rituximab supports further investigation into its clinical utility.

Introduction

The chimeric anti-CD20 antibody rituximab is being evaluated in an increasing number of disorders. After clinical efficacy was initially demonstrated against relapsed and refractory follicular/low grade non-Hodgkin's lymphoma[1], responses to rituximab have been reported in other malignant and non-malignant B-cell disorders[2]. Several mechanisms of action have been proposed including activation of apoptotic pathways[3], elaboration of cytokines and elicitation of host complement-dependent cytotoxicity (CDC) and antibody-dependent cell-mediated cytotoxicity (ADCC)[5]. Although many patients with B-cell disorders respond to rituximab, remissions are often transient[6]. More than 50% of lymphomas recurrent after rituximab treatment failed to respond the second time[7]. Mechanisms of resistance to rituximab are as yet unclear, and may include paucity or loss of target antigen[8], pharmacokinetic variations among individual patients, FcR polymorphism[9], resistance to complement activity[10], or inherent gene expression of the lymphoma[11].

beta-glucans are complex polymers of glucose with affinity for the lectin site of the CR3 receptor on leucocytes[12]. With bound beta-glucan, CR3 (CD11b) is primed to engage iC3b fragments deposited on cells by complement-activating antibodies. This receptor mediates the diapedesis of leukocytes through the endothelium and stimulates phagocytosis, degranulation and tumor cytotoxicity. Many fungi present beta-glucan or beta-glucan-like CR3 binding ligands on their cell surface. Hence, when iC3b deposition occurs, both CD11b and lectin sites become engaged, and phagocytosis and respiratory burst is triggered[13]. In contrast, tumor cells lack such molecules, and even when coated with iC3b do not generally activate CR3 and cannot activate leucocytes. Soluble forms of beta-glucan bind to lectin sites and prime both phagocytic and NK cells to kill iC3b-coated tumor targets[14].

(1→3), (1→4)-D-β-glucan (BG), a soluble, barley-derived beta-glucan has advantages over previously studied (1→3), (1→6)-β-glucans, particularly efficacy when administered orally and a good safety profile[15]. In vivo synergism between BG and the complement-fixing antibody 3F8 against human neuroblastoma xenografts[15,16] was recently demonstrated. The synergism between BG and rituximab against lymphoma is now reported.

Study Design

Cell Lines:

Human Burkitt's lymphoma cell line, Daudi, and Hodgkin's disease (HD) cell lines Hs445 and RPMI 6666 were purchased from American Type Culture Collection (Rockville, Md.). Human EBV-BLCL were established using previously described methods[17].

Mice:

Fox Chase ICR SCID mice (Taconic, White Plains, N.Y.) were maintained under institutionally approved guidelines and protocols.

Tumor Models:

Subcutaneous tumors were established by injecting $5\times10^6$ cells suspended in 0.1 ml of Matrigel (Becton-Dickinson, Franklin Lakes, N.J.) into mice flanks. Tumor dimensions were measured two to three times a week and tumor size was calculated as the product of the two largest diameters. Mice were sacrificed when maximum tumor dimension exceeded 20 mm. A disseminated tumor model was established in SCID mice as previously described[18]. Briefly, $5\times10^6$ Daudi or Hs445 cells in 100 μl normal saline were injected intravenously into SCID mice. Tumors grew systemically and mice became paralyzed when tumor cells infiltrated the spinal cord, resulting in hind-leg paralysis. Mice were sacrificed at onset of paralysis or when animals lost 10% of their body weight.

Treatment Regimens:

For mice with subcutaneous tumors, therapy was initiated after tumors were established (7-8 mm diameter). For the disseminated tumor model, therapy was initiated ten days after injection of tumor cells. Groups of at least five mice per treatment regimen received either rituximab, BG, neither or both. 200 μg rituximab (Genentech, San Francisco, Calif.) was injected intravenously twice weekly for a total of eight injections and 400 μg BG (Sigma, St. Louis, Mo.) administered orally via intragastric gavage daily for 29 days. Animals were weighed weekly and observed clinically at least once daily.

Statistical Analysis:

Tumor growth was calculated by fitting a regression slope for each individual mouse to log transformed values of tumor size. Slopes were compared between groups using t-tests using a previously described method for censored observations[19]. Survival in mice with disseminated disease was compared using Kaplan-Meier analysis and proportion of deaths was compared by Fisher's exact $\chi 2$ test. Analyses were conducted using STATA 7 (Stata Corporation, College Station, Tex.).

Results and Discussion

In all subcutaneous xenograft models, significant reduction in tumor growth was noted in mice treated with a combination of rituximab and BG. Mice treated with rituximab alone showed a modest reduction in tumor growth, while those treated with BG alone or left untreated had unabated tumor growth (FIG. 1A, 1B, 1C). All tumors except for those treated with combination therapy grew beyond 20 mm size and mice had to be sacrificed. Mice on combination treatment had persistent tumor suppression even after treatment was stopped. In a multivariable linear model of tumor growth rate, using dummy variables for treatment, the interaction between BG and rituximab was positive and significant, demonstrating synergism.

Figure 2A:
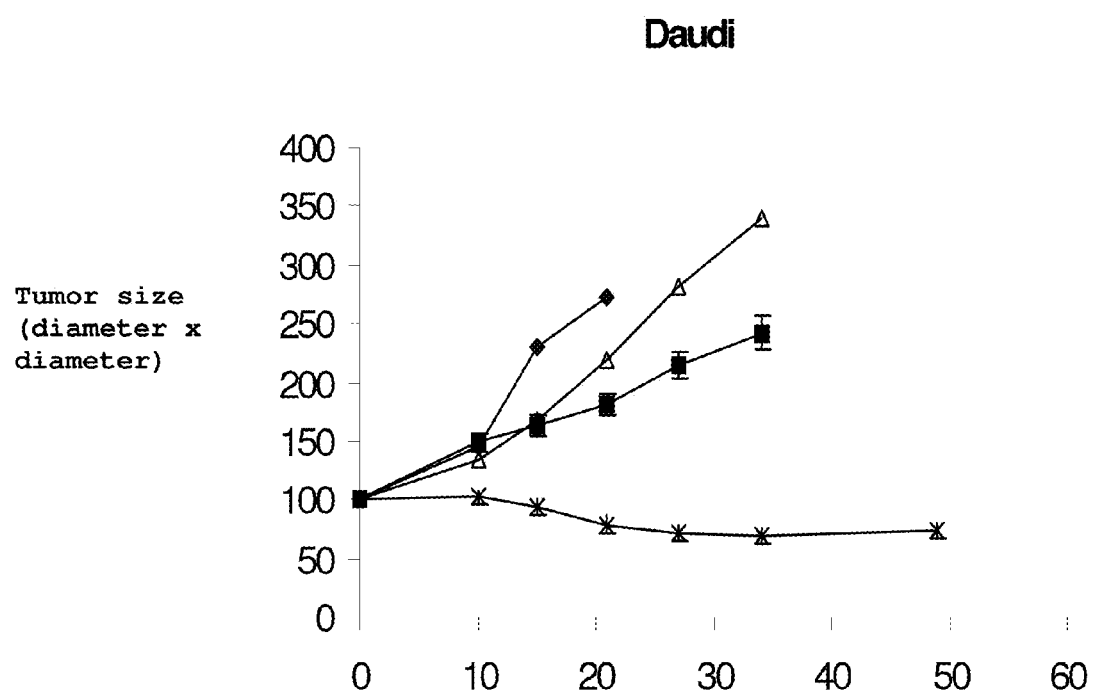
Figure 2B:
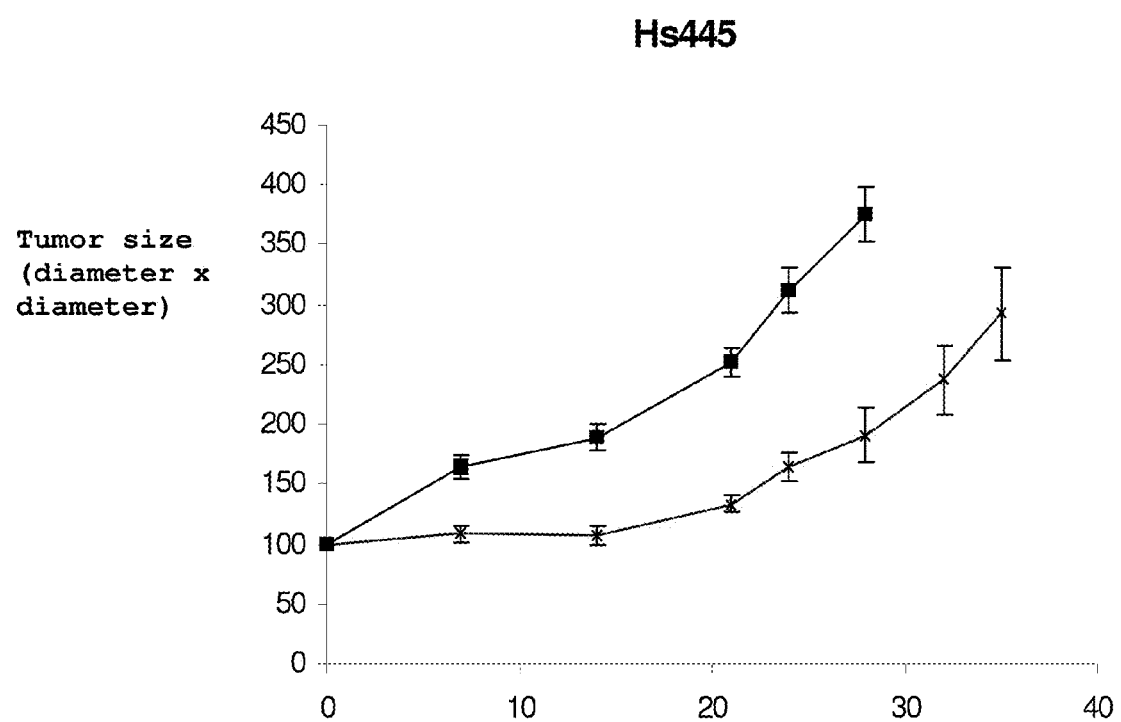
Figure 2C:
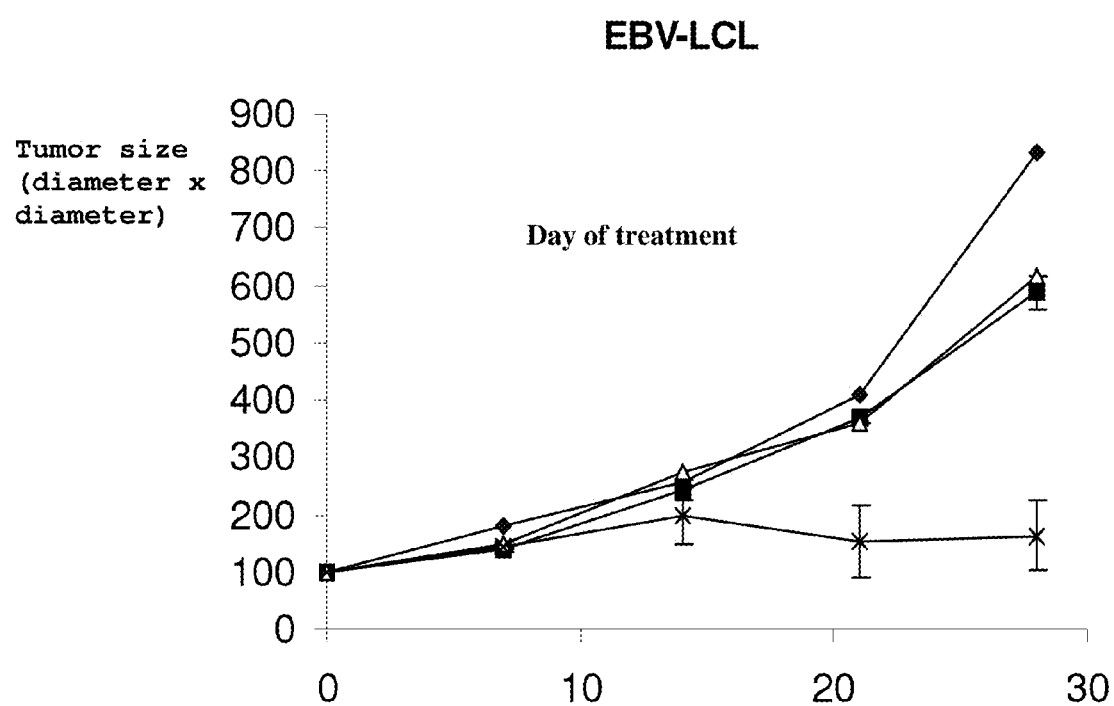
Figure 3A:
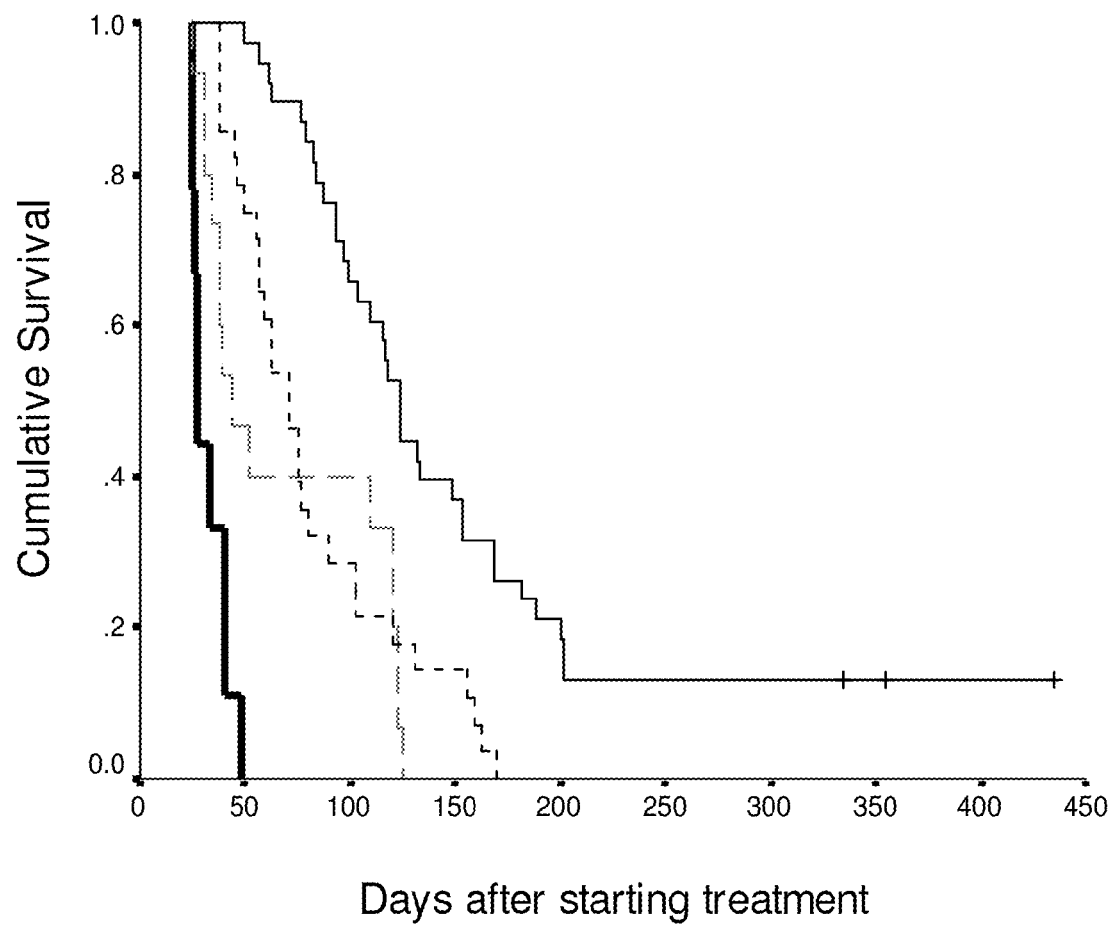
Figure 3B:
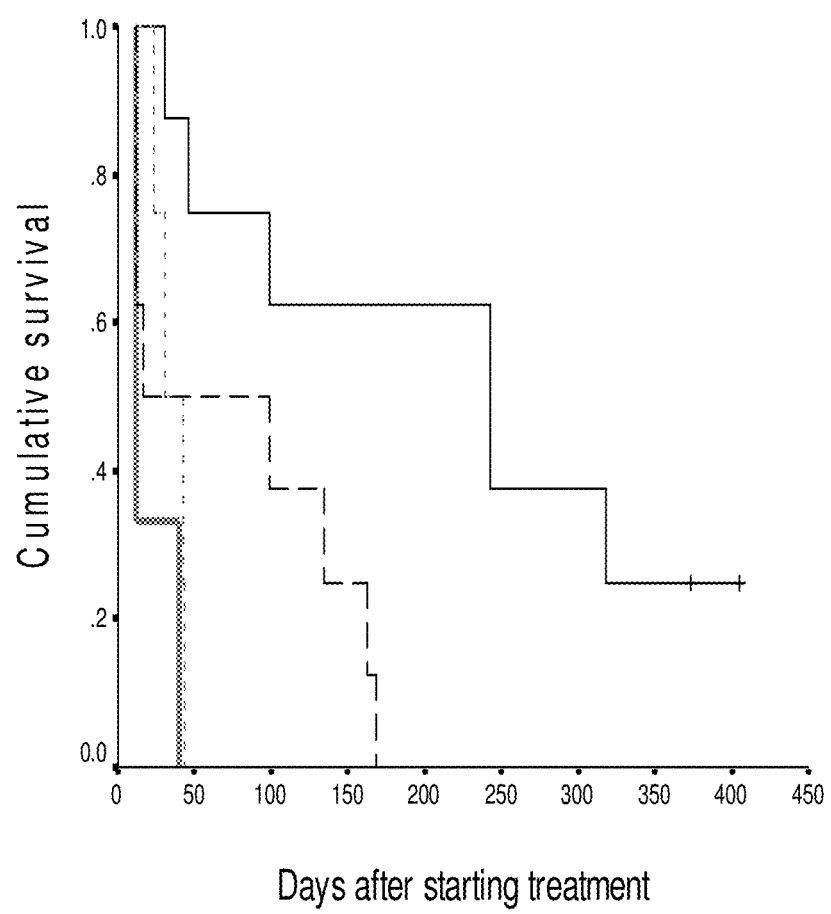

For disseminated xenografts, there was a significant difference in survival between the combination and control groups for both NHL and HD models ($p<0.005$, by log-rank) (FIG. 2). 5/38 mice and 2/8 mice with disseminated Daudi and Hs445 tumors respectively treated with combination BG and rituximab were surviving >12 months after therapy was discontinued suggesting complete eradication of disease. In contrast, 0/29 and 0/8 mice receiving rituximab alone in respective groups survived (15% vs. 0% survival; $\chi 2=0.01$). There was no significant weight loss or other clinically apparent adverse effects. That BG is absorbed can be inferred from the fact that it could be detected intracellularly within fixed and permeabilized peripheral blood leucocytes by immunofluorescence (data not shown).

In these studies, synergism between BG and rituximab was highly significant irrespective of the type of CD20-positive lymphoma. Improved responses in Daudi xenografts as compared to Hs445 may be attributable to higher CD20 expression in the former (Mean geometric fluorescence channel for Daudi 241 compared to 184 for Hs445). When tumors that progressed were examined for CD20 expression by immunofluorescence studies of single cell suspensions or indirect immunohistochemistry of frozen sections, no significant difference was noted between groups treated with rituximab, BG alone or rituximab+BG (data not shown), indicating that treatment with rituximab+BG was not associated with loss of CD20.

Synergism between other complement-activating monoclonal antibodies and BG[15,16] were previously demonstrated. The current data extend this observation to rituximab. CDC is considered an important mechanism for rituximab cytotoxicity. Rodent complement is not inhibited efficiently by human complement regulatory proteins (mCRP). Therefore CDC can be an effective anti-tumor mechanism in xenograft models. However in a study, at sub-therapeutic doses of antibody, rituximab-mediated ADCC and CDC were not sufficient to effect tumor cell killing. Since BG has no direct effect on ADCC[20], this synergy is most likely a result of iC3b-mediated tumor cytotoxicity. Lymphoma cells express mCRP including CD46, CD55, and CD59[10,21]. However, iC3b-mediated cytotoxicity is unaffected by the presence of CD59 which affects only MAC-mediated complement cytotoxicity[22]. Furthermore, in human breast carcinoma tumors, deposition of iC3b has been demonstrated despite the presence of mCRP[23] indicating that unlike their inhibitory effect on MAC, effect on iC3b-mediated tumor cytotoxicity is not absolute.

If this synergistic effect can be safely reproduced in humans, iC3b-mediated cytotoxicity may be a potential strategy to overcome rituximab resistance in patients with B-cell malignancies. Since neither T nor B cells are required for this synergistic effect, BG may have a potential role even in immunocompromised lymphoma patients. Furthermore, in patients with autoimmune disorders, B-cell depletion may be enhanced with this non-toxic oral therapy. Conversely, beta-glucans can enhance release of cytokines such as TNF-α and IL-6[24], and because the acute toxicities of rituximab are also related to cytokine release secondary to complement activation[25], there is a potential of increased toxicity when BG and rituximab are used in combination. Carefully designed phase I studies are necessary in order to define the safety and efficacy in developing BG as an adjunct to rituximab therapy in the treatment of B-cell disorders and in antibody-based therapies of other cancers.

References for Example II

1. Maloney D G, Liles T M, Czerwinski D K, Waldichuk C, Rosenberg J, Grillo-Lopez A, Levy R. Phase I clinical trial using escalating single-dose infusion of chimeric anti-CD20 monoclonal antibody (IDEC-C2B8) in patients with recurrent B-cell lymphoma. Blood. 1994; 84:2457-2466
2. Cheson B D. Rituximab: clinical development and future directions. Expert Opin Biol Ther. 2002; 2:97-110
3. Alas S, Emmanouilides C, Bonavida B. Inhibition of interleukin 10 by Rituximab results in Down-regulation of Bcl-2 and sensitization of B-cell Non-Hodgkin's lymphoma to apoptosis. Clin Cancer Res. 2001; 7:709-723
4. Chow K U, Sommerlad W D, Boehrer S, Schneider B, Seipelt G, Rummel M J, Hoelzer D, Mitrou P S, Weidmann E. Anti-CD20 antibody (IDEC-C2B8, rituximab) enhances efficacy of cytotoxic drugs on neoplastic lymphocytes in vitro: role of cytokines, complement, and caspases. Haematologica. 2002; 87:33-43
5. Reff M E, Carner K, Chambers K S, Chinn P C, Leonard J E, Raab R, Newman R A, Hanna N, Anderson DR. Depletion of B cells in vivo by a chimeric mouse human monoclonal antibody to CD20. Blood. 1994; 83:435-445
6. McLaughlin P, Grillo-Lopez A J, Kink B K, Levy R, Czuczman M S, Williams M E, Heyman M R, Bence-Bruckler I, White C A, Cabanillas F, Jain V, Ho A D, Lister J, Wey K, Shen D, Dallaire B K. Rituximab chimeric anti-CD20 monoclonal antibody therapy for relapsed indolent lymphoma: half of patients respond to four-dose treatment program. J Clin Oncol. 1998; 16:2825-2833
7. Davis T A, Grillo-Lopez A J, White C A, McLaughlin P, Czuczman M S, Link B K, Maloney D G, Weaver R L, Rosenberg J, Levy R. Rituximab anti-CD20 monoclonal antibody therapy in non-Hodgkin's lymphoma: safety and efficacy of re-treatment. J Clin Oncol. 2000; 18:3135-3143
8. Davis T A, Czerwinski D K, Levy R. Therapy of B-cell lymphoma with anti-CD20 antibodies can result in the loss of CD20 antigen expression. Clin Cancer Res. 1999; 5:611-615
9. Cartron G, Dacheux L, Salles G, Solal-Celigny P, Bardos P, Colombat P, Watier H. Therapeutic activity of humanized anti-CD20 monoclonal antibody and polymorphism in IgG Fc receptor FcgammaRIIIa gene. Blood. 2002; 99:754-758
10. Golay J, Zaffaroni L, Vaccari T, Lazzari M, Borleri G M, Bernasconi S, Tedesco F, Rambaldi A, Introna M. Biologic response of B lymphoma cells to anti-CD20 monoclonal antibody rituximab in vitro: CD55 and CD59 regulate complement-mediated cell lysis. Blood. 2000; 95:3900-3908
11. Bohen S P, Troyanskaya O G, Alter O, Warnke R, Botstein D, Brown P O, Levy R. Variation in gene expression patterns in follicular lymphoma and the response to rituximab. Proc Natl Acad Sci USA. 2003; 100:1926-1930
12. Bohn J A, BeMiller J N. (1-3)-B-D-Glucans as biological response modifiers: a review of structure-functional activity relationships. Carbohydr Polymers. 1995; 28:3-14
13. Ross G D, Cain J A, Myones B L, Newman S L, Lachmann P J. Specificity of membrane complement receptor type three (CR3) for beta-glucans. Complement Inflamm. 1987; 4:61-74
14. Xia Y, Vetvicka V, Yan J, Hanikyrova M, Mayadas T, Ross G D. The beta-glucan-binding lectin site of mouse CR3 (CD11b/CD18) and its function in generating a primed state of the receptor that mediates cytotoxic activation in response to iC3b-opsonized target cells. J. Immunol. 1999; 162:2281-2290
15. Cheung N K, Modak S. Oral (1-3),(1-4)-beta-glucan synergizes with anti-ganglioside GD2 monoclonal antibody 3F8 in the therapy of neuroblastoma. Clin Cancer Res. 2002; 8:1217-1223
16. Cheung N K, Modak S, Vickers A, Knuckles B. Orally administered beta-glucans enhance anti-tumor effects of monoclonal antibodies. Cancer Immunol Immunother. 2002; 51:557-564
17. Koehne G, Gallardo H F, Sadelain M, O'Reilly R J. Rapid selection of antigen-specific T lymphocytes by retroviral transduction. Blood. 2000; 96:109-117
18. Wei B R, Ghetie M A, Vitetta E S. The combined use of an immunotoxin and a radioimmunoconjugate to treat disseminated human B-cell lymphoma in immunodeficient mice. Clin Cancer Res. 2000; 6:631-642
19. Vardi Y, Ying Z, Zhang C—H. Two-sample tests for growth curves under dependent right censoring. Biometrika. 2001; 88:949-960
20. Yan J, Vetvicka V, Xia Y, Coxon A, Carroll M C, Mayadas T N, Ross G D. B-glucan a "Specific" biologic response modifier that uses antibodies to target tumors for cytotoxic recognition by leukocyte complement receptor type 3 (CD11b/CD18). J. Immunol. 1999; 163:3045-3052

21. Treon S P, Mitsiades C, Mitsiades N, Young G, Doss D, Schlossman R, Anderson K C. Tumor cell expression of CD59 is associated with resistance to CD20 serotherapy in patients with B-cell malignancies. J. Immunother. 2001; 24:263-271
22. Jurianz K, Ziegler S, Garcia-Schuler H, Kraus S, Bohana-Kashtan O, Fishelson Z, Kirschfink M. Complement resistance of tumor cells: basal and induced mechanisms. Mol. Immunol. 1999; 36:929-939
23. Vetvicka V, Thornton B P, Wieman T J, Ross G D. Targeting of natural killer cells to mammary carcinoma via naturally occurring tumor cell-bound iC3b and beta-glucan-primed CR3 (CD11b/CD18). J. Immunol. 1997; 159:599-605
24. Adachi Y, Okazaki M, Ohno N, Yadomae T. Enhancement of cytokine production by macrophages stimulated with (1→3)-beta-D-glucan, grifolan (GRN), isolated from *Grifola frondosa*. Biol Pharm Bull. 1994; 17:1554-1560
25. Van der Kolk L E, Grillo-Lopez A J, Baars J W, Hack C E, van Oers M H. Complement activation plays a key role in the side-effects of rituximab treatment. Br J. Haematol. 2001; 115:807-811

Example III

Barley β-Glucan Extract Synergizes with IgM Antibodies

Figure 4:
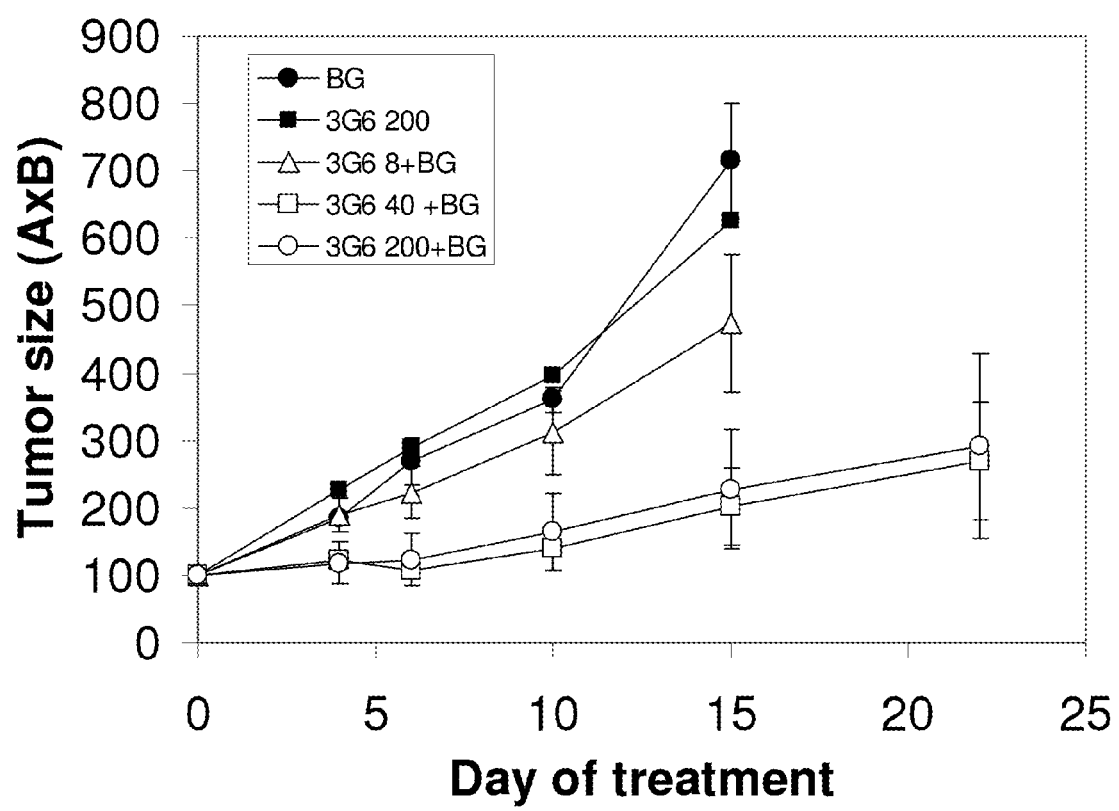

Natural IgM antibody from human serum when administered i.v. was cytotoxic for human neuroblastoma (NB) cells effecting growth arrest of subcutaneous solid human NB xenografts in nude rats.(1, 2) IgM was taken up by the tumors with massive perivascular complement activation and accumulation of granulocytes after 24 hours.(3) In metastatic NB model, IgM antibody was effective in eliminating tumors in 90% of the mice.(4) The absence of this anti-NB IgM antibody during infancy and among NB patients (of any age), and its prevalence after 12 months of age has raised the hypothesis that natural IgM antibodies could play a role as an immunological control mechanism against NB.(5) 3G6 is an anti-GD2 mouse IgM monoclonal antibody (MoAb). Within 48 hours after i.v. injection of biotinylated 3G6, subcutaneous NB xenografts showed membrane staining of tumor cells. Although 3G6 had lower mean fluorescence (53±19 fluorescent channel units, n=7 mice) when compared to 3F8, an IgG MoAb (149±44, n=7), 3G6 plus beta-glucan was effective against sc human NB (p<0.05), with a dose response curve (FIG. 4) comparable to that of 3F8.(6) These findings were consistent with those using human natural anti-NB IgM.(1, 2) These data support the idea that beta-glucan can enhance not just IgG inducing vaccines, but also IgM inducing vaccines.

References for Example III

1. David K, Ollert M W, Juhl H, et al: Growth arrest of solid human neuroblastoma xenografts in nude rats by natural IgM from healthy humans. Nat Med 2:686-9, 1996
2. Ollert M W, David K, Schmitt C, et al: Normal human serum contains a natural IgM antibody cytotoxic for human neuroblastoma cells. Proc Natl Acad Sci USA 93:4498-503, 1996
3. Ollert M W, David K, Vollmert C, et al: Mechanisms of in vivo anti-neuroblastoma activity of human natural IgM. Eur J Cancer 33:1942-8, 1997
4. Engler S, Thiel C, Forster K, et al: A novel metastatic animal model reflecting the clinical appearance of human neuroblastoma: growth arrest of orthotopic tumors by natural, cytotoxic human immunoglobulin M antibodies. Cancer Res 61:2968-73, 2001
5. Erttmann R, Schmitt C, Ollert M W, et al: Naturally occurring humoral cytotoxicity against neuroblastoma (NB) cells in healthy persons and NB patients. Pediatr Hematol Oncol 13:545-8, 1996
6. Cheung N, Modak S: Oral (1-3),(1-4)-beta-glucan synergizes with anti-ganglioside GD2 monoclonal antibody 3F8 in the therapy of neuroblastoma. Clin Cancer Res 8:1217-1223, 2002

Figure 5:
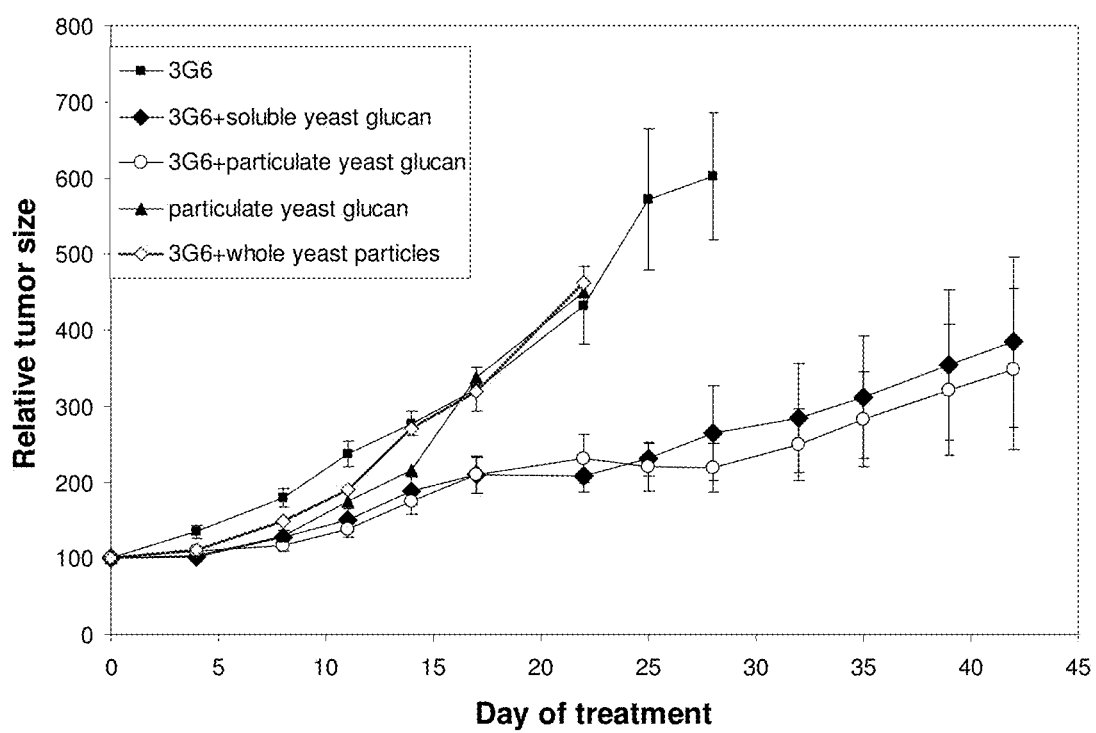
Figure 6:
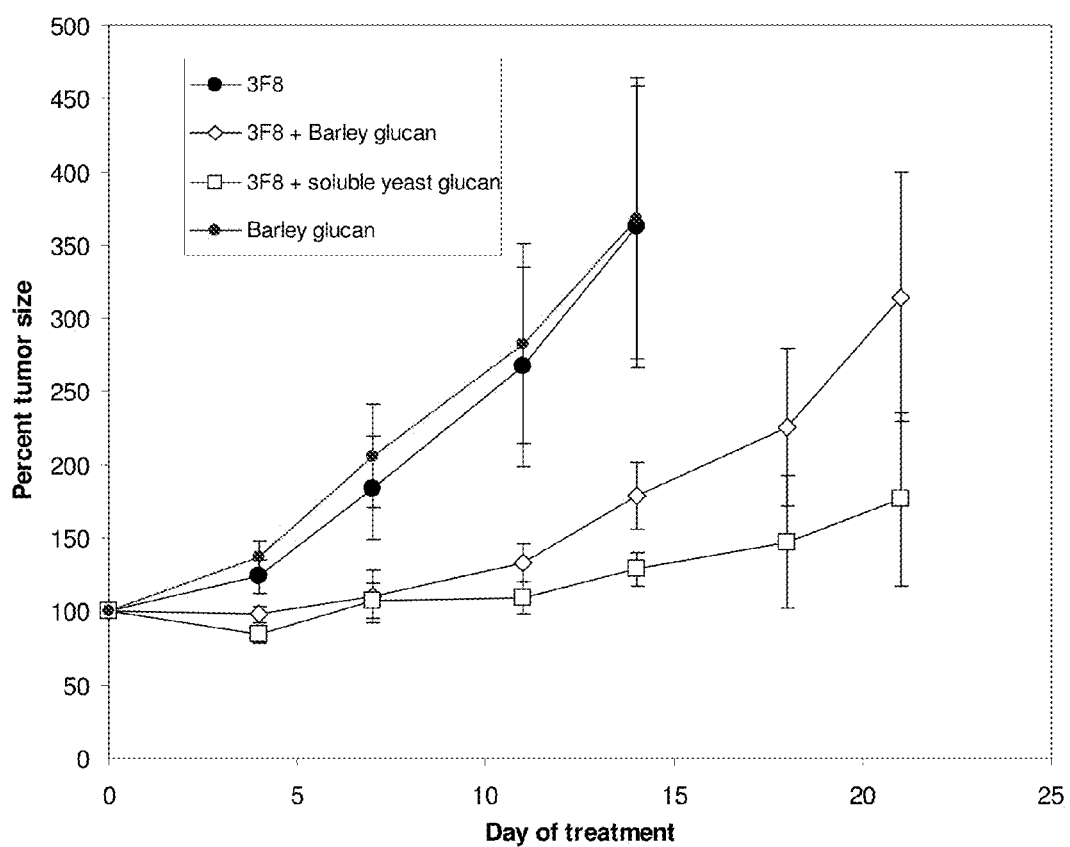

Example IV (1→3), (1→6) β-Glucan Derived from Baker's Yeast (Derived from *Saccharomyces Cerevisiae*) is Also Effective in Enhancing Antibody Therapy of Cancer LAN-1 tumor cells were planted (2×10 cells) in 100 μl of Matrigel (Sigma) subcutaneously. Tumor dimensions were measured two to three times a week with vernier calipers, and tumor size was calculated as the product of the two largest perpendicular diameters. All treatment studies started in groups of 4-5 mice when tumor diameters reached 0.7 to 0.8 cm. Mice received antibody (3F8 or 3G6) treatment (200 ug per day) i.v. (by tail vein injection) twice weekly×5 doses and oral beta-glucan (400 ug per day) by intragastric injection every day for a total 14-18 days. (See FIGS. 5 and 6)

Glucans derived from cell walls of yeasts, such as *Saccharomyces cervisiae* or mutant yeast strains described in U.S. Pat. No. 5,250,436, the disclosure of which is incorporated herein in its entirety by reference, may be used in the above compositions. Glucans having β(1-3) and β(1-6) linkages may be prepared by the process described in U.S. Pat. Nos. 5,233,491 and 4,810,646, the disclosures of which are incorporated herein in their entirety by reference. Soluble or aqueous glucans which are suitable for oral administration may be produced by the process described in U.S. Pat. Nos. 4,810, 646 and 5,519,009, the disclosures of which are incorporated herein in their entirety by reference. Beta-glucans such as the Soluble beta-1,3/1,6 glucan or SBG manufactured by Biotec Pharmacon (Norway) may also be used.

In similar experiments a subcutaneous lymphoma model was studied. Here 5×10$^6$ cells suspended in 0.1 ml of Matrigel (Becton-Dickinson, Franklin Lakes, N.J.) were planted into mice flanks. Tumor dimensions were measured two to three times a week and tumor size was calculated as product of the two largest diameters. Mice were sacrificed when maximum tumor dimension exceeded 20 mm. 200 μg rituximab (Genentech, San Francisco, Calif.) was injected intravenously twice weekly for a total of eight injections and 400 μg glucan administered orally via intragastric gavage daily for 29 days. Mice were weighed weekly and observed clinically at least once daily. The rate of tumor response and the percent of mice achieving complete remissions were comparable between barley glucan and yeast glucan. These series of subcutaneous tumor models showed that soluble yeast (1→3),(1→6) beta-glucan of large molecular weight (>10,000 Daltons) is equally potent as barley (1→3),(1→4) beta-glucan. In addition, the source and physical form of yeast glucan can make substantial differences.

Figure 7:
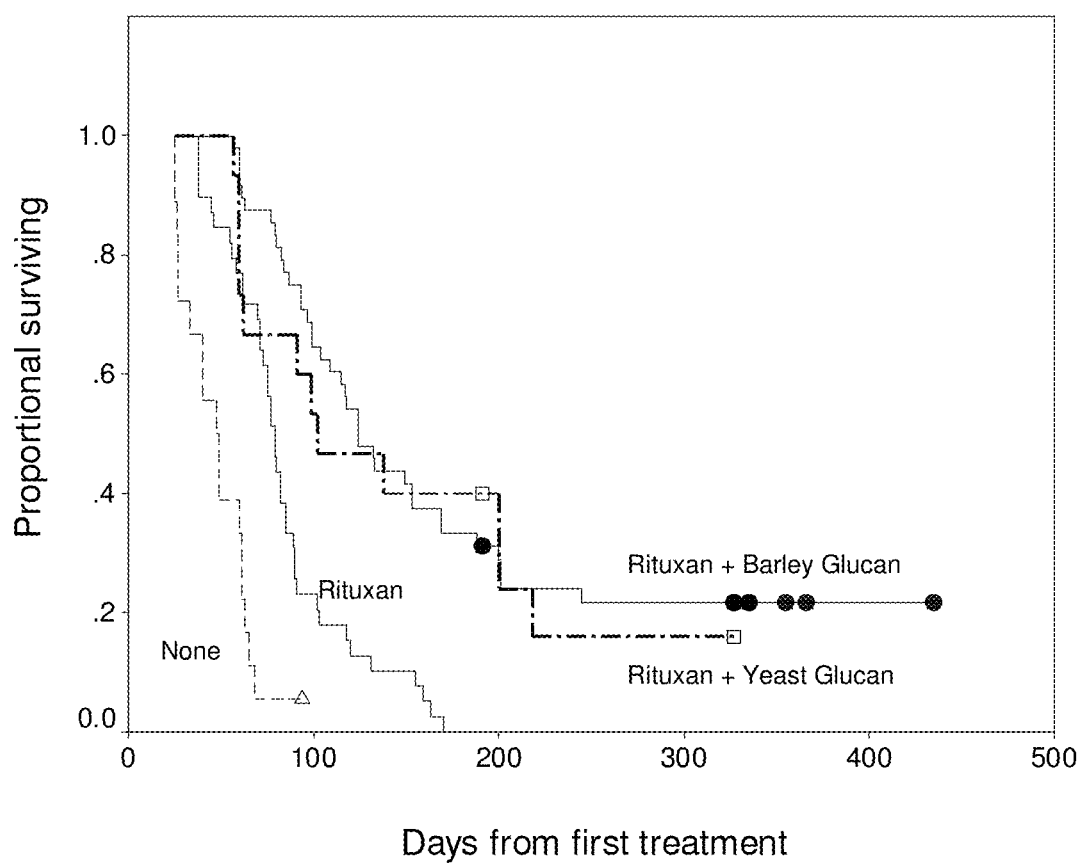

Metastatic lymphoma model was also studied. A model of disseminated tumors was established in SCID mice as previously described. (1) Briefly, 5×10$^6$ Daudi cells in 100 μl normal saline were injected intravenously (i.v.) into SCID mice. Tumors grew systemically and mice became paralyzed when tumor cells infiltrated the spinal canal, resulting in hind-leg paralysis. Mice were sacrificed at onset of paralysis or when animals lost 10% of their body weight. Therapy was initiated ten days after injection of tumor cells. 40 µg rituximab (Genentech, San Francisco, Calif.) was injected intravenously twice weekly for a total of eight injections and 400 µg glucan administered orally via intragastric gavage daily for 29 days. Mice were weighed weekly and observed clinically at least once daily. (See FIG. 7)

Again both barley glucan and yeast glucan showed comparable effect when combined with Rituxan. Neither barely glucan nor yeast glucan has any effect on survival when used alone (data not shown).

References for Example IV

1. Wei B R, Ghetie M A, Vitetta E S: The combined use of an immunotoxin and a radioimmunoconjugate to treat disseminated human B-cell lymphoma in immunodeficient mice. Clin Cancer Res 6:631-642, 2000

Example V

Mechanism by which Orally Administered β-Glucans Function with Anti-Tumor Monoclonal Antibodies to Mediate Tumor Regression.(1)

Using syngeneic tumor (GD2+ RMA-S) in wild type (WT) C57Bl/6 mice versus either CR3-deficient (CD11b−/−) or C3-deficient (C3−/−) C57Bl/6 mice, MoAb alone elicited no tumor regression, whereas combining the i.v. anti-GD2 MoAb with oral barley or yeast beta-glucan elicited significant regression in WT but not in CR3-deficient mice. Moreover, the combined treatment with i.v. MoAb and oral beta-glucans produced 60-100% tumor-free survivors in WT mice, but only 0-20% survival in the CR3-deficient mice. These experiments demonstrated a near absolute requirement for leukocyte CR3 for the anti-tumor effect, especially when oral barley beta-glucan was given with anti-tumor MoAb. A therapy protocol comparing WT to C3-deficient mice similarly showed that oral beta-glucan therapy required serum C3. When barley beta-glucan and yeast beta-glucan were labeled with fluorescein (BG-F and YG-F) and given to mice by intragastric injection, the trafficking of beta-glucan was followed. Within three days of daily oral administration of BG-F or YG-F, macrophages in the spleen and lymph nodes contained fluorescein-labeled beta-glucan. After 4 d, YG-F and BG-F were also observed in macrophages in bone marrow. When the uptake of YG-F and BG-F by WT versus CR3-deficient mice was compared, no differences were apparent in either the percentage of macrophages containing ingested beta-glucan-F or the amount of beta-glucan-F per cell. Thus, the uptake of barley and yeast beta-glucan by gastrointestinal macrophages does not require CR3 and is likely mediated instead by Dectin-1.(2) Macrophages in vitro and in the marrow were able to degrade large molecules of barley or yeast beta-glucan into smaller biologically-active fragments of beta-glucan that are then released.

To determine if the soluble beta-glucan-F released by macrophages had indeed been taken up by bone marrow granulocytes, groups of WT or CR3-deficient mice that had been given YG-F or BG-F for 10 days were injected i.p. with thioglycolate medium to elicit the marginated pool of bone marrow granulocytes into the peritoneal cavity. Only WT granulocytes were able to pick up the YG-F and BG-F released from macrophages. These data suggest a sequential ingestion of beta-glucan by gastrointestinal macrophages that shuttle the beta-glucan to the bone marrow where soluble degradation fragments are released and taken up by granulocytes via membrane CR3. When peritoneal granulocytes were isolated from WT and CR3-deficient mice that had been given oral beta-glucan, only WT granulocytes were able to kill iC3b-coated tumor cells in vitro. These experiments show that bone marrow granulocytes and tissue macrophages acquire membrane CR3-bound soluble beta-glucan from gastrointestinal macrophages, and that this bound beta-glucan primes the CR3 of both granulocytes and macrophages so that when they are recruited to a site of inflammation they are able to kill iC3b-coated tumor cells.

References for Example V

1. Hong F, Yan J, Baran J T, et al: Mechanism by which orally administered beta(1,3)-glucans function with anti-tumor monoclonal antibodies to mediate tumor regression and tumor-free survival. J Exp Med, 2004
2. Herre J, Gordon S, Brown G D: Dectin-1 and its role in the recognition of beta-glucans by macrophages. Mol Immunol 40:869-76, 2004

Example VI

Soluble β-Glucan can be Used as a Conduit for Plasmids

The major obstacles for the delivery of DNA, RNA and proteins orally are the acidic and proteolytic environment of the stomach, and limited uptake of proteins by the GALT. It is believed that M cells within the Peyer's patches and phagocytes are the predominant vehicles for uptake of microparticulates. However, nanoparticles may also access GALT via a paracellular mechanism[1,2] and by transcytosis.[3] In either case, particle uptake observed can be improved using particles with mucoadhesive properties or affinity for receptors on cells. Many polymers have been used to fabricate nanoparticles are mucoadhesive. Among them are alginate, carrageenans, and pectin. Although these materials were often used as the core polymers in nanoparticulates, no specific receptor has been identified for these polymers and the efficiency of uptake remains suboptimal. Dectin-1 is now known to be a universal receptor for β-glucan, and is found in many human tissues including monocytes and phagocytes. The gelling properties of high molecular weight β-glucan allows RNA, DNA and proteins to be embedded. Since sugars are highly resistant to acid conditions and enzymes, proteins, RNA and DNA remain protected during their passage through the gastrointestinal tract. Through the high affinity Dectin-1 receptor for β-glucan, these substances can be introduced into the phagocytes as potential vehicles to the rest of the body.

Figure 8:
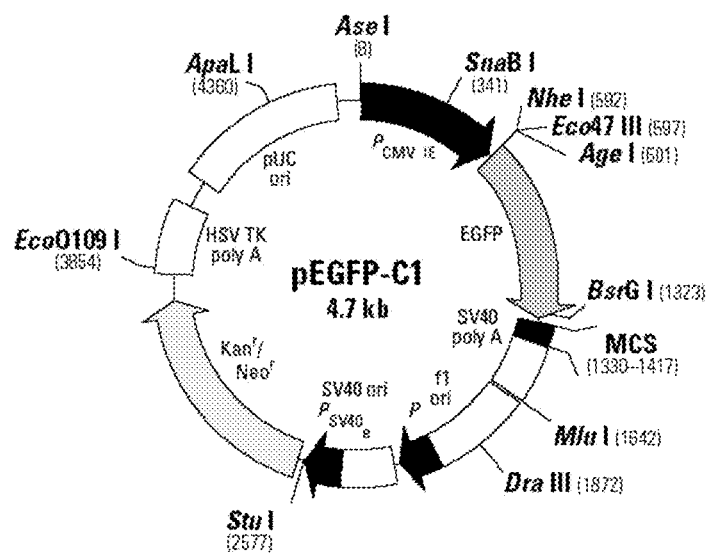
FIG. 8 illustrates the pEGP-C1 vector purchased from BD Biosciences (Palo Alto, Calif.).

The pEGP-C1 vector (See FIG. 8) was purchased from BD Biosciences (Palo Alto, Calif.) and prepared according to manufacturers' instructions. pEGFP-C1 encodes a red-shifted variant of wild-type GFP (1-3) which has been optimized for brighter fluorescence and higher expression in mammalian cells. (Excitation maximum=488 nm; emission maximum=507 nm.) The vector backbone also contains an SV40 origin for replication in mammalian cells only if they express the SV40 T-antigen. A bacterial promoter upstream of this cassette expresses kanamycin resistance in *E. coli*. The pEGFP-C1 backbone also provides a pUC origin of replication for propagation in *E. coli* and an f1 origin for single-stranded DNA production.

Figure 9:
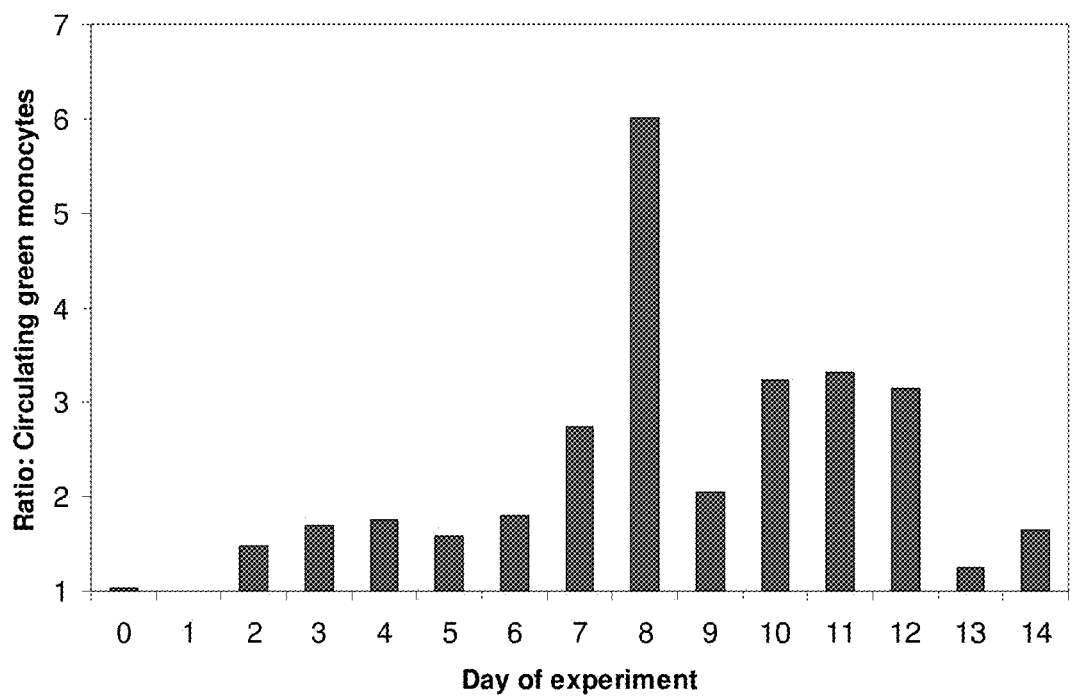
FIG. 9 shows glucan facilitates gene transfer into monocytes.

Mice were fed with 50 µg pEGFP-c1 plasmid mixed into 400 µg beta-glucan (~200,000 Daltons) in 100 µl saline by oral gavage while control mice were given plasmid alone. Oral feeding was done for 3 consecutive days (days 1, 2 and 3). 50 µl blood taken from tail vein were analysed by FCAS analysis after lysis of RBC and the % of GFP-expressing cells in the monocyte population were recorded. The mean ratio of % green cells in glucan versus no glucan groups (n=4-9 mice per group) is presented in FIG. 9. Throughout the 14 days of the experiment, % green monocytes in the no-glucan group remained stable at background levels. On the other hand, after day 1 of oral gavage, there was a consistent higher % of circulating green monocytes, which peaked around day 8. Since the GFP is not normally found in mouse monocytes, the presence of green cells is consistent with GFP protein expression following entry of the plasmid into the monocytes which circulate in the blood.

Figure 10:
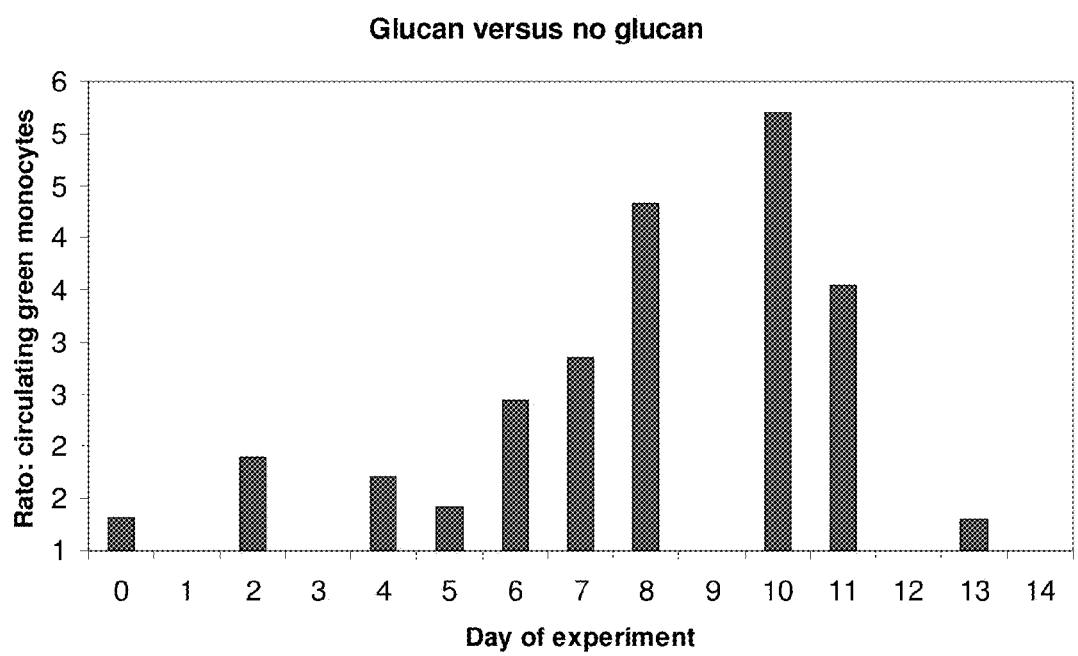
FIG. 10 illustrates higher molecular weight β-glucan and gene transfer.

The experiment was repeated using barley β-glucan of higher molecular weight (~350,000 Daltons) with better gelling properties. In FIG. 10, similar kinetics was seen, with a higher percent of green cells that persisted from day 8 through day 11 (n=4 mice per group).

Figure 11:
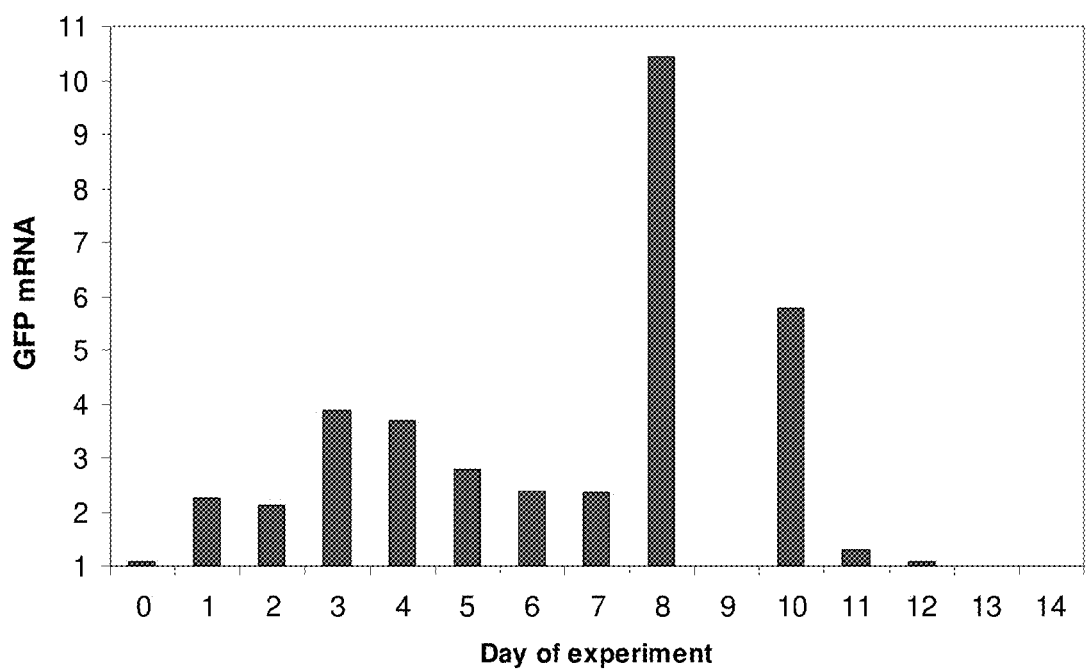
FIG. 11 illustrates presence of GFP mRNA in circulating monocytes.

Presence of GFP mRNA was tested using quantitative reverse-transcription PCR analysis. Mice were fed with 50 μg pEGFP-c1 plasmid mixed into 400 μg high molecular weight (350,000 Daltons) beta-glucan in 100 μl saline by oral gavage while control mice were given plasmid alone. 50 μl peripheral blood was used to extract total RNA, reverse transcribed and quantitative real-time PCR was performed using a modification of the method previously described.[4] The house keeping gene mouse GAPDH is used as internal control. Transcript level is calculated using a known GFP and GAPDH standard. Transcript units are calculated separately for GFP and GAPDH and results as a ratio of GFP over GAPDH. In FIG. 11, the mean RNA level (GFP/GAPDH) is expressed as a ratio of glucan versus no glucan groups (n=4 mice per group). GFP mRNA was detected up to day 10.

References for Example VI

1. Damge C, Aprahamian M, Marchais H, et al: Intestinal absorption of PLAGA microspheres in the rat. J Anat 189 (Pt 3):491-501, 1996
2. Jani P, Halbert G W, Langridge J, et al: Nanoparticle uptake by the rat gastrointestinal mucosa: quantitation and particle size dependency. J Pharm Pharmacol 42:821-6, 1990
3. Florence A T: The oral absorption of micro- and nanoparticulates: neither exceptional nor unusual. Pharm Res 14:259-66, 1997
4. Cheung I Y, Lo Piccolo M S, Collins N, et al: Quantitation of GD2 synthase mRNA by real-time reverse transcription-polymerase chain reaction: utility in bone marrow purging of neuroblastoma by anti-GD2 antibody 3F8. Cancer 94:3042-8, 2002

What is claimed is:

1. A method of treating cancer in a subject, comprising administering to said subject a soluble β-glucan in an amount effective to treat said cancer, wherein said glucan is derived from yeast and comprises a β-1,3 backbone with branches attached to the backbone via β-1,6 linkages, wherein the glucose units in said branches are β-1,3 linked, and said cancer is selected from the group consisting of neuroblastoma, melanoma, non-Hodgkin's lymphoma, breast cancer, non-small cell lung cancer, colorectal cancer, Epstein-Barr related lymphoma, Hodgkin's lymphoma, and epidermoid carcinoma.

2. The method of claim 1, wherein said glucan has a molecular weight of 10-350 kDa.

3. The method of claim 1, wherein said glucan is administered orally or intravenously.

4. The method of claim 1, wherein said glucan is administered at about 25 mg/kg/day.

5. The method of claim 1, further comprising administering a complement-activating antibody.

6. The method of claim 5, wherein said antibody is a monoclonal antibody.

7. The method of claim 5, wherein said antibody is administered simultaneously or sequentially with said glucan.

8. The method of claim 5, wherein said antibody is selected from the group consisting of cetuximab, M195, Dacluzimab, R24, Herceptin, Rituximab, 528, IgG, IgM, IgA, C225, Epratuzumab and 3F8.

9. The method of claim 5, wherein said antibody is cetuximab for treating non-small cell lung cancer.

10. The method of claim 5, wherein said antibody is cetuximab for treating colorectal cancer.

11. The method of claim 5, wherein said antibody is rituximab for treating non-Hodgkin's lymphoma.

12. The method of claim 1, further comprising administering a chemotherapeutic agent.

13. The method of claim 12, wherein said chemotherapeutic agent is carboplatin.

14. The method of claim 12, wherein said chemotherapeutic agent is irinotecan.

15. The method of claim 12, wherein said chemotherapeutic agent is paclitaxel.

16. The method of claim 12, wherein said glucan has a molecular weight of 10-350 kDa.

17. The method of claim 12, wherein said glucan is administered orally or intravenously.

18. The method of claim 12, wherein said glucan is administered at about 25 mg/kg/day.

SEQUENCE LISTING

```
<160> NUMBER OF SEQ ID NOS: 1

<210> SEQ ID NO 1
<211> LENGTH: 94
<212> TYPE: DNA
<213> ORGANISM: Artificial Sequence
<220> FEATURE:
<223> OTHER INFORMATION: EGFP Portion of pEGFP-C1 Vector

<400> SEQUENCE: 1

TACAAGTCCG GACTCAGATC TCGAGCTCAA GCTTCGAATT CTGCAGTCGA CGGTACCGCG      60

GGCCCGGGAT CCACCGGATC TAGATAACTG ATCA                                 94
```

19. The method of claim 12, wherein said chemotherapeutic agent is administered simultaneously or sequentially with said glucan.

20. The method of claim 12, wherein the cancer is non-small cell lung cancer.

* * * * *